US006448086B1

(12) United States Patent
Khosravi et al.

(10) Patent No.: US 6,448,086 B1
(45) Date of Patent: Sep. 10, 2002

(54) INSULIN-LIKE GROWTH FACTOR SYSTEM AND CANCER

(75) Inventors: M. Javad Khosravi; Anastasia Diamandi, both of Toronto (CA); Jehangir Mistry, League City, TX (US)

(73) Assignee: Diagnostic Systems Laboratories, Inc., Webster, TX (US)

( * ) Notice: Subject to any disclaimer, the term of this patent is extended or adjusted under 35 U.S.C. 154(b) by 0 days.

(21) Appl. No.: 09/484,903

(22) Filed: Jan. 18, 2000

(51) Int. Cl.$^7$ ...................... G01N 33/48; G01N 33/574; G01N 33/53; C12Q 1/00

(52) U.S. Cl. ............................ 436/64; 436/813; 435/4; 435/7.1; 435/7.23

(58) Field of Search ....................... 436/64, 813; 435/4, 435/7.1

(56) References Cited

FOREIGN PATENT DOCUMENTS

| EP | 0 905 142 A | 3/1999 |
|---|---|---|
| WO | WO 99 38011 A | 7/1999 |
| WO | WO 99 46597 A | 9/1999 |

OTHER PUBLICATIONS

Baciuchka et al., "Insulin–Like Growth (IGF)–Binding Protein–3 (IGFBP–3) Proteolysis in Patients with Colorectal Cancer: Possible Association with the Metastatic Potential of the Tumor," Int. J. Cancer (Pred. Oncol.) (1998) 79:460–467.
Baserga, Renato, "The Insulin–like Growth Factor I Receptor: A Key to Tumor Growth?" Cancer Research (1995) 55:249–252.
Carter et al., "The Prostate: An Increasing Medical Problem," Prostate (1990) 16:39–48.
Catalona et al., "Prostate Cancer Detection in Men With Serum PSA Concentrations of 2.6 to 4.0 ng/mL and Benign Prostate Examination: Enhancement of Specificity With Free PSA Measurements," JAMA (1997) 277(18):1452–1455.
Catalona et al., "Use of the Percentage of Free Prostate–Specific Antigen to Enhance Differentiation of Prostate Cancer From Benign Prostatic Disease: A Prospective Multicenter Clinical Trial," JAMA (1998) 279(19):1542–1547.
Cats et al., "Increased Epithelial Cell Proliferation in the Colon of Patients with Acromegaly," Cancer Research (1996) 56:523–526.
Chan et al., "Plasma Insulin–Like Growth Factor–I and Prostate Cancer Risk: A Prospective Study," Science (1998) 279:563–566.
Chen et al., "Prostate Specific Antigen in Benign Prostatic Hyperplasia: Purification and Characterization," J. of Urology (1997) 157:2166–2170.

Cho et al., "Expression of Alpha–1 antichymotrypsin in Prostate Carcinoma," J Korean Med Sci. (1997) 12(3):228–33 1997.
Cohen, Pinchas, "Serum Insulin–Like Growth Factor–I Levels and Prostate Cancer Risk–Interpreting the Evidence," J. of Natl Cancer Inst. (1998) 90(12):876–879.
Cohen et al., "Physiologic and clinical relevance of the insulin–like growth factor binding proteins," Current Opinion in Pediatrics, (1994) 6:462–467.
Cohen et al., "Prostate–Specific Antigen (PSA) is an Insulin–Like Growth Factor Binding Protein–3 Protease Found in Seminal Plasma," J. Clinical Endocrinology & Metabolism (1992) 75(4):1046–1053.
Colao et al., "Effect of Growth Hormone (GH) and Insulin–Like Growth Factor I on Prostate Diseases; Au Untrasonographic and Endocrine study in Acromegaly, GH Deficiency, and Healthy Subjects," J. Clinical Endocrinology & Metabolism (1999) 84(5):1986–1991.
Diamandi et al., "Immunoassay of Insulin–Like Growth Factor–Binding Protein–3 (IGFBP–3): New Means to Quantifying IGFBP–3 Proteolysis," J. Clinical Endocrinology & Metabolish (2000) 85(6):1–2.
Diamandis et al., "Specificity of New Immunoassays for Human Insulin–Like Growth Factor (IGF) Binding Protein–3 (IGFBP–3)," Proceedings of the 80th Annual Meeting of the Endrocine Society (Jun. 24–27, 1998) Abstract P3–360.
Diamandis, Eleftherios P., "Prostate–specific Antigen: Its Usefulness in Clinical Medicine," Elsevier Science Ltd (1998) 9(8):310–316.
Ferry, Jr. et al., "Insulin–Like Growth Factor Binding Proteins: New Proteins, New Functions," Horm Res (1999) 51:53–67.
Giudice, Linda C., "Editorial: IGF Binding Protein–3 Protease Regulation: How Sweet It Is!," J. of Clinical Endocrinology & Metabolism 80(8):2279–2281.
Glick et al., "Insulin–like growth factors in central nervous system tumors," J. Neuro–Oncology (1997) 35:315–325.
Grimberg et al., "Growth hormone and prostate cancer: Guilty by association?" J. Endocrinol. Invest. (1999) 22:64–73.
Hankinson et al., "Circulating concentrations of insulin–like growth factor–I and risk of breast cancer," Lancet (1998) 351 (9113):1373–1374.

(List continued on next page.)

Primary Examiner—Anthony C. Caputa
Assistant Examiner—Gary B. Nickol
(74) Attorney, Agent, or Firm—Haynes and Boone, LLP

(57) ABSTRACT

Method of monitoring or diagnosing disease conditions, including disease of the prostate, that involve measuring a combination of tumor markers and at least one component of the IGF axis. The invention is exemplified with prostate cancer and benign prostatic hyperplasia, the tumor marker prostate specific antigen, and the insulin-like growth factors and their binding proteins.

4 Claims, 8 Drawing Sheets-

OTHER PUBLICATIONS

Harrela et al., "Genetic and Environmental Components of Interindividual Variation in Circulating levels of IGF–1, IGF–II, IGFBP–1, and IGFBP–3," J. Clin. Invest. (1996) 98(11):2612–2615.

Holly, Jeff, "Insulin–like growth factor–I and new opportunities for cancer prevention," Lancet (1998) 351(9113):1393–1396.

Hwa et al., "Insulin–like growth factor binding proteins: a proposed superfamily," Acta Pediatr Suppl (1999) 428:37–45.

Jones et al., "Insulin–Like Growth Facors and Their Binding proteins: Biological Actions," Endocrine Reviews (1995) 16(1):3–34.

Juul et al., "The ratio between serum levels of insulin–like growth factor (IGF)–I and the IGF binding proteins (IGFBP–1, 2 and 3) decreases wtih age in healthy adults and is increased in acromegalic patients," Clinical Endocrinology (1994) 41:85–93.

Kao et al., "Insulin–Like Growth Factor–I Comparisons in Healthy Twin Children," J. Clinical Endocrinology & Metabolism (1994) 78(2):310–312.

Kelley et al., "Insulin–like Growth Factor–binding Proteins (IGFBPs) and Their Regulatory Dynamics," Int. J. Biochem. Cell Biol. (1996) 28:617–637.

Khosravi et al., "The High Molecular Weight Insulin–Like Growth Factor–Binding Protein Complex: Epitope Mapping, Immunoassay, and Preliminary Clinical Evaluation," J. Clinical Endocrinology & Metabolism (1999) 84(8):2826–2833.

Khosravi et al., "Noncompetitive ELISA for human serum insulin–like growth factor–I," Clinical Chemistry (1996) 42(8):1147–1154.

Khosravi et al., "Factors Influencing Immunoassay Levels of Free Insulin–Like Growth Factors as Determined by New ELISAs," Proceedings of the 80th Annual Meeting of the Endrocrine Society (Jun. 24–27, 1998) Abstract P3–355.

Khosravi et al., "Immunoassay of insulin–like growth factor of binding protein–I," Clinical Chemistry (1997) 43(3):523–532.

Lahm et al., "Blockage of the Insulin–Like Growth–Factor–I Recewptor Inhibits Growth of Human Colorectal Cancer Cells: Evidence of a Functional IGF–II–Mediated Autocrine Loop," Int. J. Cancer (1994) 58:452–459.

Lamson et al., "Insulin–Like Growth Factor Binding Proteins: Structural and Molecular Relationships," Growth Factors, (1991) 5:19–28.

Lee et al., "Active Insulin–Like Growth Factor–I (IFG–I) Assays," Technical Release, Diagnostic Systems Laboratories, Inc. pp. 1–8.

Li et al., "Expression of insulin–like growth factor (IGF)–II in human prostate, breast, bladder, and paraganglioma tumors," Cell Tissue Res (1998) 291:469–479.

Luderer et al., "Measurement of the Proportion of Free to Total Prostate–Specific Antigen Improves Diagnostic Performance of Prostate–Specific Antigen in the Diagnostic Gray Zone of Total Prostate–Specific Antigen," Urology (1995) 46(2):187–194.

Manousos et al., "IGF–I and IGF–II in Relation to Colorectal Cancer," Int. J. Cancer (1999) 83:15–17.

Oh, Youngman, "IGF–independent regulation of breast cancer growth by IGF binding proteins," Breast Cancer Research and Treatment (1998) 47:283–293.

Orme et al., "Mortality and Cancer Incidence in Acromegaly: A Retrospective Cohort Study," J. Clinical Endocrinology & Metabolism (1998) 83(8):2730–2734.

Rajah et al., "Insulin–like Growth Factor (IGF)–binding Protein–3 Induces Apoptosis and Mediates the Effects of Transforming Growth Factor–β1 on Programmed Cell Death through a p53– and IGF–independent Mechanism," J. Biological Chemistry (1997) 272(18):12181–12188.

Rajah et al., "Insulin–Like Growth Factor Binding Protein (IGFBP) Proteases: Functional Regulators of Cell Growth," Progress in Growth Factor Research (1995) 6(2–24):273–284.

Rajaram et al., "Insulin–Like Growth Factor–Binding Proteins in Serum and Other Biological Fluids: Regulation and Functions," Endocrine Reviews (1997) 18(6):801–831.

Rechler, Matthew M., "Editorial: Growth Inhibition by Insulin–Like Growth Facotr (IGF) Binding Protein–3— What's IGF Got To Do With It?" Endocrinology (1977) 138(7):2645–2647.

Rosen et al., "Circulating IGF–I: New perspectives for a New Century," Elsevier Science (1999) 10(4):136–141.

Russell et al., "Growth factor involvement in progression of prostate cancer," Clinical Chemistry (1998) 44(4):705–723.

Sauter et al., "Insulin–Like Growth Factor Binding Protein Type 3 (IGFBP–3) is Associated with Breast Cancer Risk," Cancer Epidemiology Biomarkers and Prev (submitted) (1999) pp. 1–20.

Stenman et al., "A Complex Between Prostate–specific Antigen and $\alpha_1$–Antichymotrypsin Is the Major Form of Prostate–specific Antigen in Serum of Patients with Prostatic Cancer: Assay of the Complex Improves Clinical Sensitivity for Cancer," Cancer Research (1991) 51:222–226.

Thissen et al., "Nutritional Regulation of the Insulin–Like Growth Factors," Endocrine Reviews (1994) 15(1):80–101.

Valentinis et al., "The Human Insulin–Like Growth Factor (IGF) Binding Protein–3 Inhibits the Growth of Fibroblasts with a Targeted Disruption of the IGF–I Receptor Gene," Molecular Endocrinology (1995) 9:361–367.

Wolk et al., "Insulin–Like Growth Factor I and Prostate Cancer Risk: a Population–Based, Case–Control Study," J. of Natl Cancer Inst. (1998) 90(12):911–915.

Woodrum et al., "Analytical performance of the Tandem®–R free PSA immunoassay measuring free prostate–specific antigen," Clinical Chemistry (1997) 43(7):1203–1208.

Yu et al., "Insulin–Like Growth Factor–Binding Protein–3 and Breast Cancer Survival," Int. J. Cancer (Pred. Oncol.) (1998) 79:624–628.

Yu et al., "Plasma Levels of Insulin–Like Growth Factor–I and Lung Cancer Risk: a Case–Control Analysis," J. Natl Cancer Inst. (1999) 91(2):151–156.

Yu et al., "Insulin–Like Growth Factors (IGF–I, Free IGF–I, and IGF–II) and Insulin–Like Growth Factor Binding Proteins (IGFBP–2, IGFBP–3, and IGFBP–6 and ALS) in Blood Circulation," J. Clinical Lab Analysis (1999) 13:166–172.

Zadeh et al., "The 16–kDa Proteolytic Fragment of Insulin–like Growth Factor (IGF) Binding Protein–3 Inhibits the Mitogenic Action of Fibroblast Growth Factor on Mouse Fibroblasts with a Targeted Disruption of the Type 1 IFG Receptor Gene," Endocrinology (1997) 138(7):3069–3072.

Djavan B., et al., "Insulin–Like Growth Factor 1 (IGF–1 Density, and IGF–1/PSA Ratio For Prostate Cancer Detection," Urology, vol. 54, No. 4, Oct. 1999 (1999–10), pp. 603–606, XP000986913 ISSN: 0090–4295.

Seitz C., et al., "Insulin–Like Growth Factor 1 (IGF–1), IGF 1 Density of the Prostate (IGFD) and IGF to PSA Ratio (IGF/PSA) as New Tools for Prostate Cancer Detection," Journal of Urology, vol. 161, No. 4 Suppl., Apr. 1999 (1999–04), p. 321, XP000986922 94th Annual Meeting of the American Urological Association, Inc.; Dallas, Texas, USA; May 1–6, 1999 ISSN: 0022–5347.

INSULIN-LIKE GROWTH FACTOR SYSTEM AND CANCER

BACKGROUND

1. Field of the Invention

This invention relates to the measurement of the IGF-axis component levels and tumor marker levels for use in assessing cancer risk and/or progression and/or distinguishing between cancer and other non-malignant disorders. The invention is exemplified with prostate cancer (CaP) and benign prostatic hyperplasia (BHP), the tumor marker prostate specific antigen (PSA), and the insulin-like growth factors (IGF) and their binding proteins (IGFBP). Specifically, IGF-I, intact IGFBP-3, fragment IGFBP-3, total IGFBP-3, free PSA and total PSA were assayed and certain permutations of these measurements were found to present improved diagnostic indicators. The method is predicted to have general applicability to other IGF-system related cancers.

2. Description of the Prior Art

The insulin-like growth factor (IGF) family of high affinity IGF binding proteins (IGFBP-1–6) (1–4) has recently evolved to a superfamily status in order to accommodate a related group of newly discovered low affinity IGFBPs called the IGFBP related proteins (5). The conventional view of IGFBPs as the sole regulators of IGF bioavailability and bioactivity has also evolved to include the IGF-independent properties of IGFBPs (6, 7). IGFBPs, particularly IGFBP-3, have been recently identified as potent apoptotic agents (8–12), presumably mediating the effects of cellular growth suppressing mechanisms (8, 11, 12). The emerging new concept appears to similarly broaden the pathophysiological roles of the IGF peptides to include their potential involvement in regulation of the IGFBPs' bioactivity (8). In this ever-expanding maze of reciprocal molecular interactions, post-translational modification by selective proteolysis is rapidly gaining acceptance as the key modulator of the IGF/IGFBP system and a major determinant of their effects on cellular growth and metabolism (13, 14).

Insulin-like growth factors (IGF-I and -II) are mitogenic and anti-apoptotic agents produced primarily by the liver and locally by a wide variety of tissues. IGFs circulate mostly complexed with IGFBP-3, which in association with the acid-labile subunit (ALS) forms an approximately 150 kD ternary protein complex (1–4). Under normal conditions, nearly all of the circulating IGFs remain ternary complexed (75–80%), and smaller proportions (20–25%) are associated with the low molecular weight IGFBPs (IGFBP-1, IGFBP-2, IGFBP4, IGFBP-5, and IGFBP-6) or exist in the free form (1–4).

Dysregulation and/or over-expression of the IGF system have been long implicated in the etiology of both benign and malignant proliferative disorders (3, 4, 15–19). Malignant cells of various origins have been shown to express various components of the IGF system (3, 4, 11–13, 18–22), and increased IGF-I levels, as seen in acromegaly, have been found in association with benign prostatic hyperplasia (BPH) (23, 24) and colonic tumors (25, 26). High levels of circulating IGF-I has been more recently identified as risk factors for the development of prostate, breast, and lung cancers (27–30), while over-expression of both IGF-I and IGF-II has been linked to colorectal cancers (31). In prostate, both benign and malignant cells have been found to express IGFs, IGFBPs and their respective receptors (18, 23). IGF-I has been shown to promote prostate cell growth, while prostate specific antigen (PSA) has been identified as an IGFBP-3 protease, presumably capable of augmenting tissue access to the IGF peptides (18, 23, 32).

In men over 50 years of age, cancer of the prostate (CaP) and benign prostatic hyperplasia (BPH) are among the most commonly diagnosed malignant and benign proliferative disorders, respectively (33). However, serum levels of PSA, the most reliable predictor of CaP available to date, is also increased in BPH, resulting in a diagnostic "gray-zone" in the PSA range of ~4–10 $\mu$g/L (34). In addition, PSA levels of less than 4 $\mu$g/L does not necessarily indicate disease-free status because significant numbers of men with organ-confined CaP reportedly express normal PSA levels (35). These significant limitations of PSA testing invariably result in a diagnostic dilemma, allowing for loss opportunity for early cancer detection, or unnecessary surgical approaches to a readily treatable benign disorder. Although the ratio of free/total PSA levels in serum is significantly reduced in CaP and its determination is now used to heighten the diagnostic accuracy of PSA testing (36, 37), there is still a great need to further improve our ability to discriminate between BPH and prostate cancer (35).

SUMMARY OF THE INVENTION

Abbreviations and Definitions

ACT—alpha-1-antichymotrypsin.

ALS—Acid Labile Subunit. A protein found in the 150 kD ternary complex wherein most of the circulating IGF-I is found. ALS is sensitive to inactivation by acid, urea and certain detergents.

Body fluid—Any biological fluid, including but not limited to the following: serum, plasma, lymph fluid, synovial fluid, follicular fluid, seminal fluid, amniotic fluid, milk, mammary fluid, whole blood, urine, spinal fluid, saliva, sputum, tears, perspiration, mucus, tissue culture medium, tissue extracts and cellular extracts. Preferably, the body fluid is blood, plasma, serum or seminal fluid.

BHP—benign prostatic hyperplasia.

CaP—cancer of the prostate.

DHT—Dihydrotestosterone.

GH—Growth hormone.

GHBP—GH binding protein.

IGF—Insulin-like Growth Factor.

IGF-axis components—Those components that modulate the IGF/GH cascades including GH, GHBP, GH receptor, IGF I and II, IGF receptors, IGF proteases, IGFBP-1 through -6 and the IGFBP related proteins IGFBP-rP-1–9, IGFBP proteases, ALS, IGF and GH receptor antagonists, and the like. Altered levels of IGF axis components are known to be associated with a variety of malignant diseases, including breast, ovarian, endometrial, colorectal and prostate cancer, as discussed herein, and also with papillary thyroid cancer, Wilms tumor and possibly other CNS tumors, choroid plexus papilloma, meningiomas, hepatocellular carcinoma, rhabdomyosarcoma, gastric carcinomas, liver cancer, and colon cancer, leukemias, pituitary adenomas and tumors, and lung cancer.

IGFBP—Any IGF binding protein, including IGFBP-1 to 6 and the IGFBP related proteins IGFBP-rP-1 to 9.

IGFBP-3—The major circulating IGF binding protein. Intact IGFBP-3 refers to that portion of the total IGFBP-3 which is undegraded (and exists mainly in complexed form). Fragment IGFBP-3 refers to the fragmented forms of IGFBP-3. With the assay described herein, amino terminal fragments of IGFBP-3 that lack the carboxyl terminal amino acids are detected as fragment IGFBP-3.

Total IGFBP-3 refers to complexed, uncomplexed, intact and fragmented IGFBP-3. The various forms of IGFBP-3 are referred to collectively as "IGFBP-3 variants."

Indicator ratio—As used herein a ratio of the measured levels of IGF axis components with or without kallikrein-like components, such as PSA, which is useful to distinguish between benign and cancerous conditions or useful in monitoring the progression of a cancerous disease. The specification teaches how to evaluate various permutations of measurements of IGF axis components and tumor markers and test for clinically significant associations. For example, an indicator ratio of IGF-I/free PSA means the concentration of IGF-I divided by the concentration of free PSA.

Kallikrein—A group of serine proteases with homology to PSA, including at least K1, K2, and preprokallikreins. "Kallikrein-like proteins" includes the kallikreins and various forms of PSA.

PSA—Prostate specific antigen. Free PSA is the fraction of PSA that is not complexed with other proteins, such as ACT. Total PSA is free PSA and complexed PSA.

Ratio—Any ratio referred to herein expressly refers to and includes the inverse ratio. Thus if the ratio of IGF-I/free PSA is informative about a particular disease state, of course the ratio of free PSA/IGF-I will be equally informative.

SHBG—Sex hormone binding globulin.

T—Testosterone.

Tumor Marker—As used herein, the term includes any marker associated with tumors or tumor progression, including PSA and kallikrein. Other tumor markers are known, measurements of any of which may be combinable with measurements of IGF axis components to provide increased discriminating power. An exemplary listing of potential tumor markers that might be useful together with measurement of IGF axis components includes: S-100 protein, C219, GCDFP-15/gp17, riboflavin carrier protein (RCP) and other vitamin carrier proteins (VCP), human chorionic gonadotropin (hCG), alpha-fetoprotein (AFP), lactate dehydrogenase, cytokeratin 19 fragment (CK19) or CYFRA21-1, carbohydrate antigen 19.9 (CA19.9), macrophage-colony stimulating factor (M-CSF), abnormal prothrombin (PIVKA-II), tissue polypeptide antigen (TPA), carcinoembryonic antigen (CEA), cancer antigen (CA) 125, CA72-4, CA15-3, squamous cell antigen (SCC), neuron specific enolase (NSE), focal adhesion kinase (FAK), soluble CD44 (sCD44), soluble CD30 (sCD30), tissue polypeptide specific antigen (TPSA), total alkaline phosphatase (T-ALP), urinary Dpd/creatinine (Cre) ratios, bone specific alkaline phosphatase (B-ALP), N-acetylneuraminic (Neu5Ac), vascular endothelial growth factor (VEGF), glutathione peroxidase, melanoma antigen (MAGE), mesothelin and megakaryocyte potentiating factor (MPF), cyclin-dependent kinase inhibitor p27 (Kip 1), PGP9.5, proliferating cell nuclear antigen (PCNA), Cyclin D1, epidermal Growth Factor (EGF), transforming growth factor alpha (TGF alpha), estrogen receptor-related protein (ERRP), multidrug resistance marker (MDRM), protein kinase C (PKC), Gs alpha, inhibin, cathepsin D, H19, the steroid hormones, p53, and cytokines and interleukins.

The invention in its broadest sense consists of a method of predicting cancer in a patient measuring at least two IGF axis components and a tumor marker. The measurements are combined in statistically significant permutations, as described herein, to provide an improved means of discriminating between cancerous and non-cancerous conditions.

More particularly, the invention provides a diagnostic tool for discriminating between benign and malignant disease. The tool is an indicator ratio which is a concentration ratio such as IGF/kallikrein-like protein, IGFBP/kallikrein-like protein, IGF/IGFBP/kallikrein-like protein, (intact IGFBP/total IGFBP)/kallikrein-like protein, and (IGF+IGFBP)/kallikrein-like protein.

The indicator ratio may also be IGF-I/free PSA, intact IGFBP-3/free PSA, (IGF-I/total IGFBP-3)/free PSA, (intact IGFBP-3/total IGFBP-3)/free PSA, and (IGF-I+intact IGFBP-3)/free PSA. It has also been discovered that intact IGFBP-3 is a valid indicator of prostate CaP and this marker may be used alone or may be combined with existing tumor marker measurements or ratios, such as free PSA or free/total PSA. The diagnostic tool can distinguish between benign conditions and lung cancer, breast cancer, colon cancer or prostate cancer.

The tool can also be used in method of predicting cancer in a patient, wherein the method comprises the determination of one or more of the above indicator ratios. The indicator ratio is compared to the ratio obtained in a normal patient population and significant deviations from the norm indicate cancer. The method can also be used to monitor the progression of disease.

DETAILED DESCRIPTION OF THE INVENTION

Figure 1A:
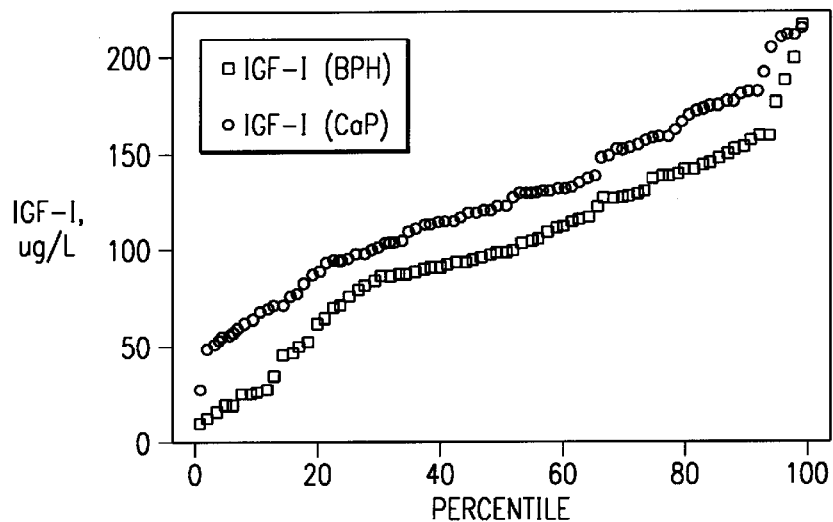
FIG. 1. Percentile distribution plots. Percentile distribution of IGF-I (FIG. 1A), intact IGFBP-3 (FIG. 1B), and free PSA (FIG. 1C) levels measured in patients with BPH (n=75) and CaP (n=84) are shown.

Generally speaking, the invention is directed to improved diagnostic indicators of malignant disease states which involve measurement of various permutations of IGF axis components together with tumor markers in order to provide increased diagnostic accuracy. The invention is exemplified with prostate cancer and the analytes: IGF-I, intact, fragment and total IGFBP-3, and free and total PSA. However, the invention can be broadened to other IGF axis components and possibly to other tumor markers as well. If other tumor markers prove useful in the way that PSA and IGF axis components have proved useful, then the invention will be applicable to other cancers, and several reasonable predictions in this regard are provided.

Specifically, the permutations of IGF-I/free PSA, intact IGFBP-3/free PSA, (IGF-I/total IGFBP-3)/free PSA, (intact IGFBP-3/total IGFBP-3)/free PSA, and (IGF-I+intact IGFBP-3)/free PSA and measurement of intact IGFBP-3 alone have been shown to be useful indicators of prostate cancer. Further, these indicator ratios together with the ratio of free/total PSA in multivariate analysis provides improved discriminating potential than does the ration of free/total PSA alone.

Example 1

In view of the growing evidence describing association of the IGF system with cancer, we used prostate cancer as a model and investigated differences in serum levels of IGF-I and intact, fragment and total IGFBP-3 in a group of patients with BPH and CaP. The age-matched patient populations were carefully selected to have total PSA in the diagnostic gray-zone range. Because of the highly complex nature of the IGF regulation, particularly involving proteolysis (13, 14), we postulated that investigation of IGF-I and IGFBP-3 variants in relation to levels of PSA in serum might help identify innovative approaches for enhancing differential BPH cancer detection. As the IGF system appears to be more widely associated with malignancy (3, 4, 11–13, 18–22), we further speculated that the present approach could have broader application in human cancer diagnostics and monitoring.

Patient Population and Samples

Serum samples from 159 patients with benign prostatic hyperplasia (BPH, 75 males aged 55–75; mean age ±SD, 65.6±6.0) or prostate cancer (84 males aged 52–75; mean age ±SD, 64.8±6.2) were provided by Dr. E. P. Diamandis Mount Sinai Hospital, Toronto, Ontario). The samples were from patients with total PSA levels between 1.75–13.5 μg/L and with histologically confirmed disease status at biopsy. All specimens were residuals from routine or research test samples and were stored frozen at −70° C., with less than three freeze/thawing cycles prior to analysis.

Analytical Methods

IGF-I, intact IGFBP-3, fragment IGFBP-3 and total IGFBP-3 were assayed by ACTIVE enzyme-linked immunosorbent assay (ELISA) kits manufactured by Diagnostic Systems Laboratories, Inc. (DSL, Inc., Webster, Tex.). These assays are based on non-competitive ELISA involving a solid-phase capture antibody and a soluble horseradish peroxidase (HRP)-labeled detection antibody. The DSL IGF-I ELISA employed is a modification of a previously described method involving acid-ethanol extraction (38, 39) and measures total IGF-I. The assay incorporates a 101-fold sample pretreatment (acid-neutralization) dilution factor and a total incubation time of less than 3 hours, and demonstrates an overall variance of less than 10% (39, 40).

The intact, fragment and total IGFBP-3 ELISAs were developed based on our knowledge of antibody binding specificity and IGFBP-3 complex epitope recognition derived by systematic evaluation of 10 different IGFBP-3 monoclonal antibodies in four different binding experiments (41), including further performance assessment using a polyclonal detection antibody. The IGFBP-3 ELISAs incorporate identical components and protocols, and involve a common monoclonal capture antibody in combination with a polyclonal (ELISA-3) or two different monoclonal (ELISA-1 and -2) detection antibodies in a manner previously reported for development of total and non-phosphorylated IGFBP-1 (42). These assays also include a 101-fold sample pre-dilution and total incubation times of about 3 hours, and their analytical specification and performance characteristics have been recently described (43, 44).

Concentrations of free and total PSA were determined by the Hybritech Tandem-R total and free (45) non-competitive immunoradiometric (IRMA) methods (Hybritech Inc., San Diego, Calif.).

Data Analysis

The ELISA results were analyzed using the data reduction packages included in the Labsystems Multiskan microplate ELISA reader (Labsystems, Helsinki, Finland) with cubic spline (smoothed) curve fit.

The analysis of differences between IGF-I and IGFBP-3 concentrations in the two groups of subjects was performed with nonparametric Mann-Whitney U test. Association of IGF-I and IGFBP-3 variants in serum with the other continuous parameters was examined using Spearman correlation. Receiver operating characteristics (ROC) curves were plotted as 1—Specificity (1−[true negatives/true negatives+ false positives] on the x axis) versus sensitivity (true positives/true positives+false negatives on the y axis) and the areas under the ROC curves (AUC) were calculated. Univariate and multivariate unconditional logistic regression models were developed to evaluate the ability of IGF-I and IGFBP-3 levels to predict the presence of prostate cancer. The plots were established by StatView (Abacus Concepts Inc, Berkeley Calif. 94704-1014). The statistical analysis was performed by SigmaStat (Superior Performing Software Systems Inc, Chicago Ill. 60606-9653) and SAS (SAS Institute, Cary, N.C. 27513).

IGF System Components in BPH vs CaP

In serum samples from a group of subjects with total PSA in the range of 1.75–13.5 μg/L we identified significantly higher IGF-I and intact IGFBP-3 levels in those with CaP than BPH (p<0.001), while changes in fragment and total IGFBP-3 were statistically insignificant (Table 1).

TABLE 1

Descriptive statistics of measured variables

| Variable[a] | BPH Subjects | | | Cap subjects | | | |
|---|---|---|---|---|---|---|---|
| | Mean | SE | Range | Mean | SE | Range | P |
| (t) PSA | 5.04 | 0.168 | 2.61–12.1 | 4.85 | 0.200 | 13.5–1.75 | 0.173 |
| (f) PSA | 1.01 | 0.056 | 0.31–3.15 | 0.757 | 0.049 | 0.15–2.59 | <0.001 |
| IGF-I | 101.2 | 5.45 | 10.9–220 | 126.6 | 4.89 | 28.0–218 | <0.001 |
| (i) BP-3 | 1.12 | 0.072 | 0.14–2.71 | 1.48 | 0.068 | 0.32–2.78 | <0.001 |
| (f) BP-3 | 3.62 | 0.192 | 1.4–9.8 | 3.39 | 0.168 | 1.19–7.81 | 0.257 |
| (t) BP-3 | 2.07 | 0.061 | 0.81–2.91 | 2.22 | 0.061 | 1.17–4.10 | 0.091 |

[a]Values for total (t) PSA, free (f) PSA, IGF-I are in μg/L; intact (i) IGFBP-3 (BP-3), fragment (f) IGFBP-3 and total (t) IGFBP-3 are in mg/L
SE = Standard error of the mean; P = probability In these samples, the mean (±SE) IGF-I and intact IGFBP-3 levels were 101.2±5.45 μg/L (range 10.9–220) and 1.12±0.072 mg/L (range 0.14–2.71) in BPH, and 126.6±4.89 μg/L (range 28–218) and 1.48±0.068 mg/L (range 0.32–2.78) in CaP patients. As expected (36), the total PSA levels were relatively similar, while free PSA showed statistically significant differences, and were 1.01±0.056 μg/L (range 0.31–3.15) and 0.757±0.049 μg/L (range 0.15–2.59) in BPH and CaP patients, respectively.

Figure 1B:
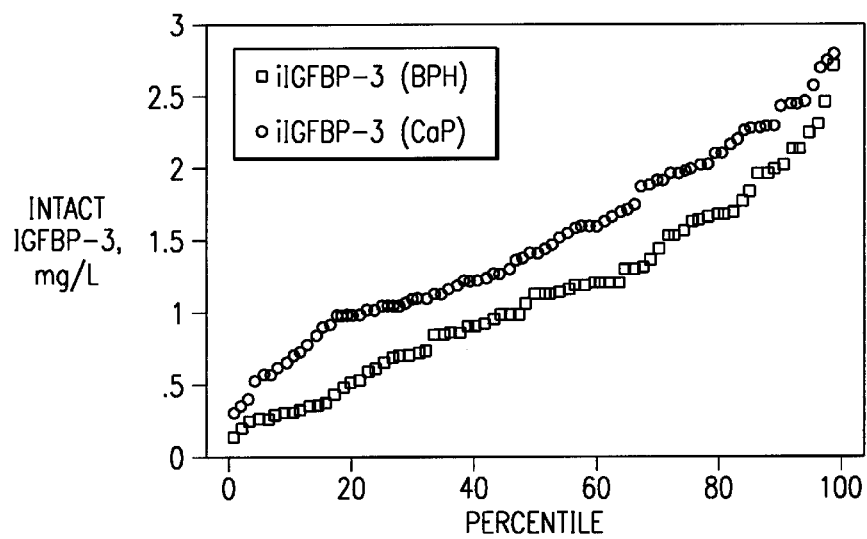
Figure 1C:
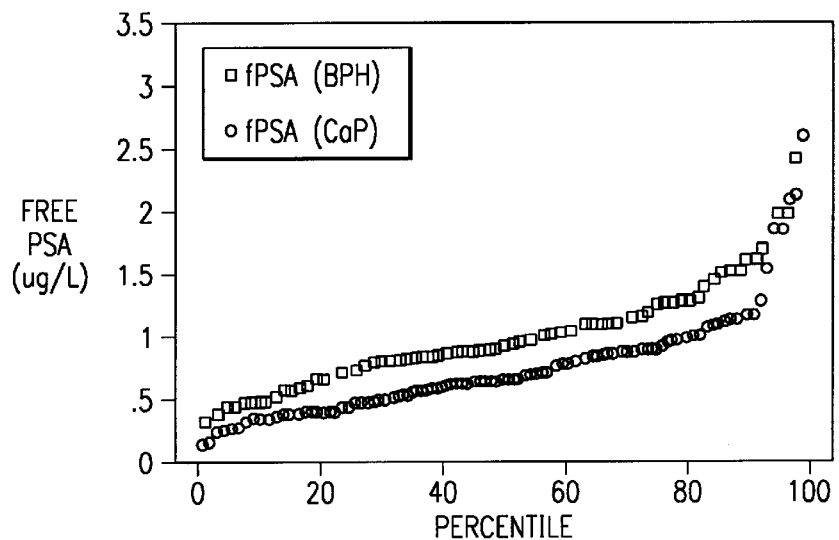

Differences in IGF-I and intact IGFBP-3 levels in BPH vs CaP were further evident in percentile distribution plots, which for the most part identified clear separation between the two groups of patients. Only at the high end of the distribution plots, the IGF-I as well as the intact IGFBP-3 levels in BPH and CaP appeared to overlap. The percentile plots of the free PSA levels demonstrated a similar but inverse pattern in relation to BPH vs CaP patients (FIG. 1). Percentile plots for total IGFBP-3, fragment IGFBP-3 and total PSA were non-discriminative and showed complete overlap throughout the range of the measurements (data not shown).

Figure 2A:
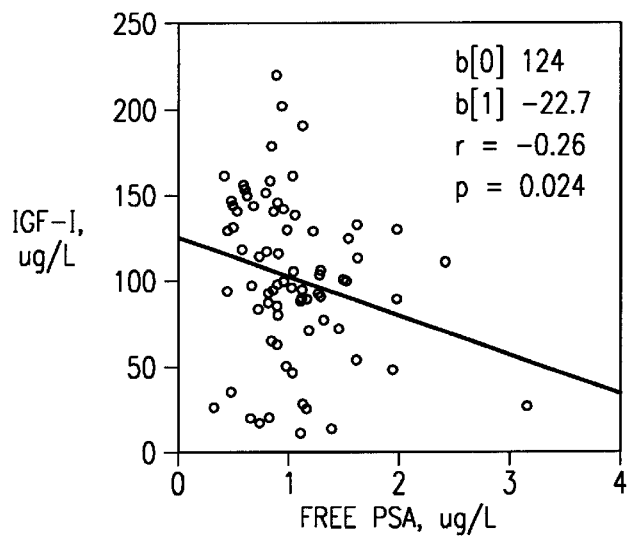
FIG. 2. Relationship of IGF-I, intact, and total IGFBP-3 with free PSA. Correlation of IGF-I (FIG. 2A), total IGFBP-3 (FIG. 2B) and intact IGFBP-3 (FIG. 2C) levels in subjects with BPH vs the corresponding free PSA levels are shown. Values are mean of duplicate measurements.
Figure 2B:
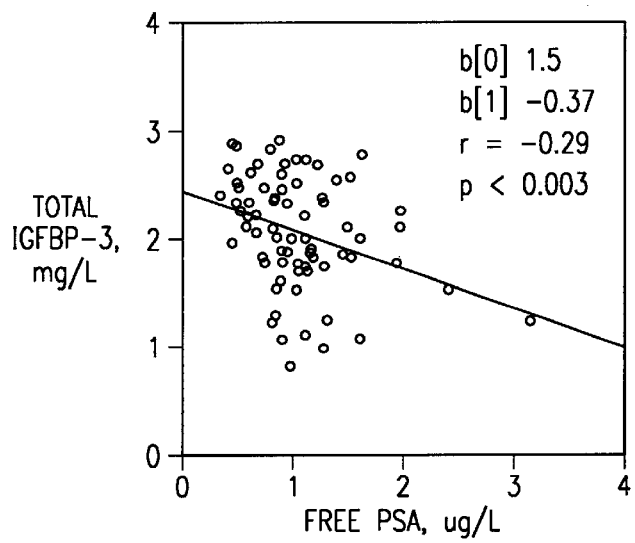
Figure 2C:
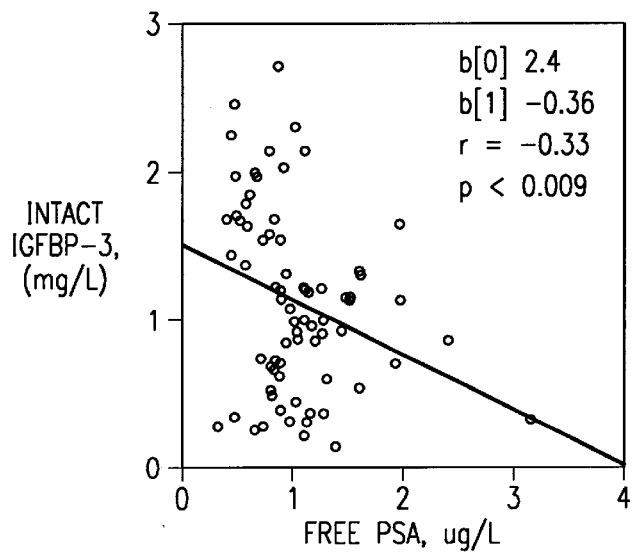
Figure 3A:
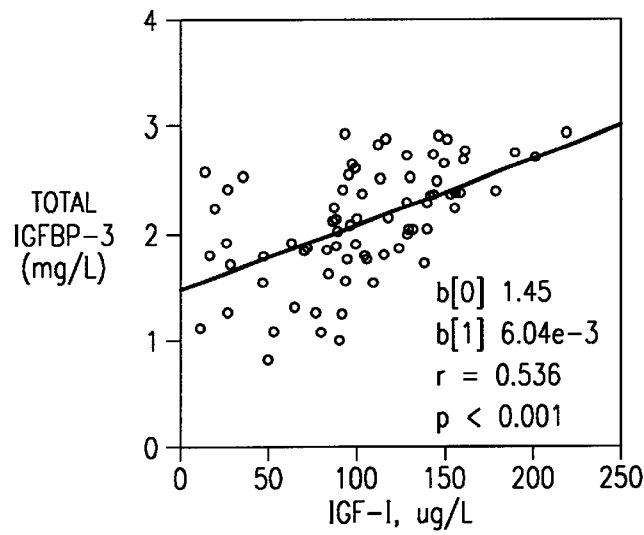
FIG. 3. Relationship of intact, fragment and total IGFBP-3 with IGF-I. Correlation of total IGFBP-3 (FIG. 3A), intact IGFBP-3 (FIG. 3B), and fragment IGFBP-3 (FIG. 3C) levels measured in subjects with BPH vs the corresponding IGF-I levels are shown. Values are mean of duplicate measurements.
Figure 3B:
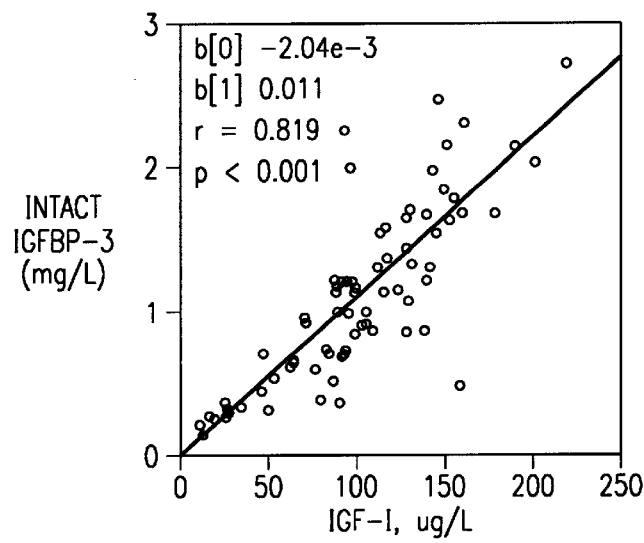
Figure 3C:
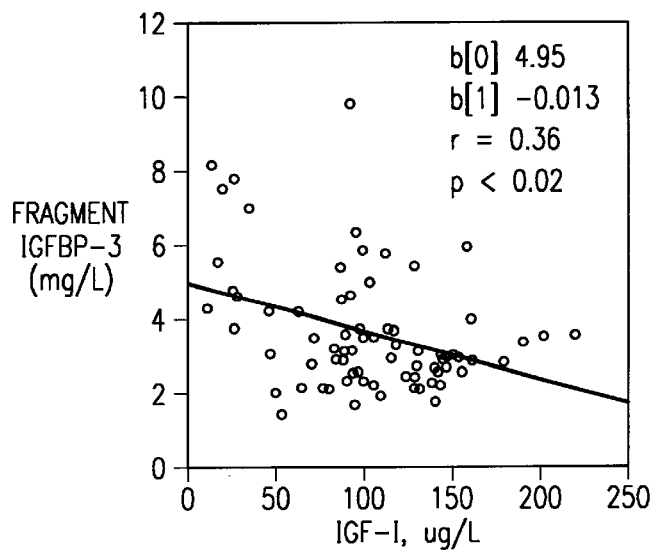
Figure 4A:
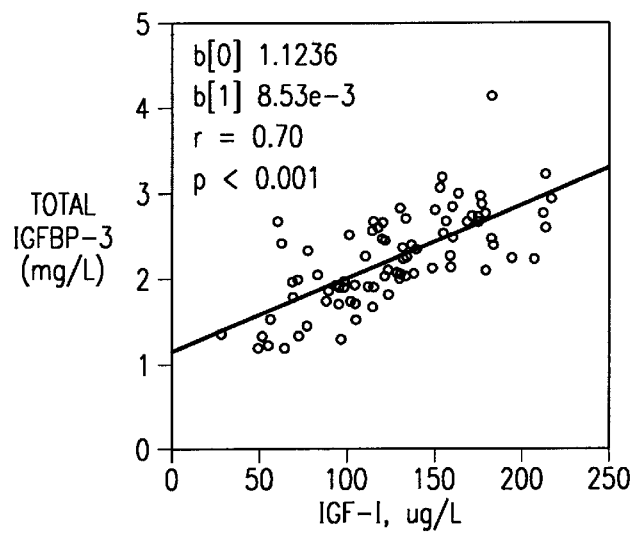
FIG. 4. Relationship of intact, fragment and total IGFBP-3 with IGF-I. Correlation of total IGFBP-3 (FIG. 4A), intact IGFBP-3 (FIG. 4B), and fragment IGFBP-3 (FIG. 4C) levels measured in subjects with CaP vs the corresponding IGF-I levels are shown. Values are mean of duplicate measurements.
Figure 4B:
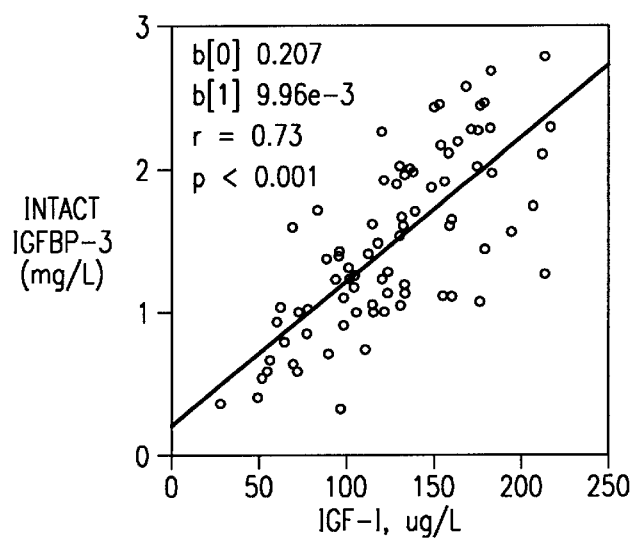
Figure 4C:
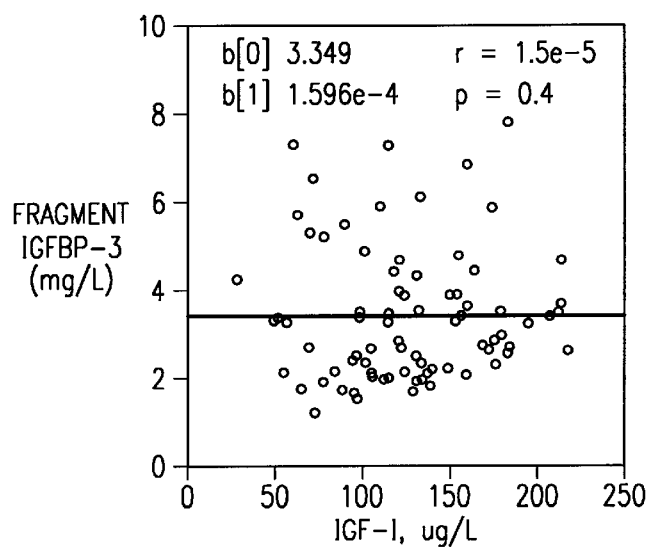

In comparative correlation analysis (Spearman), neither IGF-I nor IGFBP-3 variants correlated significantly with the corresponding total or free PSA levels detected in CaP subjects (Table 2). Similarly, IGF-I and IGFBP-3 variants did not demonstrate any significant correlation in relation to the total PSA levels in BPH (Table 2). In contrast, BPH levels of IGF-I, intact and total IGFBP-3 showed negative correlation (Spearman correlation) vs the corresponding free PSA levels (R=−0.261–0.351, p=0.024–<0.001) (Table 2). Similar results were obtained when the data were subjected to linear regression analysis by the Least-Squares method, and correlation coefficient determined by the Pearson method (FIG. 2A–2C). Interestingly, in BPH and CaP patients, IGF-I levels correlated more tightly with intact IGFBP-3 than with total IGFBP-3, while fragment IGFBP-3 was negatively related to IGF-I in BPH and not at all in CaP (FIGS. 3A–3C and 4A–4C).

TABLE 2

Correlation matrix for IGF-I and IGFBP-3 comparison to PSA[a]

| Comparative method | IGF-I | (i) BP-3 | (f) BP-3 | (t) BP-3 |
|---|---|---|---|---|
| | BPH subjects | | | |
| (t) PSA | | | | |
| r | −0.203 | −0.126 | −0.109 | −0.167 |
| p | 0.083 | 0.286 | 0.359 | 0.158 |
| (f) PSA | | | | |
| r | −0.261 | −0.308 | −0.096 | −0.351 |
| p | 0.025 | 0.008 | 0.418 | 0.0025 |
| | CaP subjects | | | |
| (t) PSA | | | | |
| r | 0.0192 | −0.069 | 0.021 | −0.004 |
| p | 0.864 | 0.540 | 0.857 | 0.974 |
| (f) PSA | | | | |
| r | −0.058 | −0.190 | 0.019 | −0.083 |
| p | 0.604 | 0.0821 | 0.866 | 0.462 |

[a]Spearman correlation

Calculated Parameters

The inverse relation of IGF-I and intact IGFBP-3 versus free PSA, and their apparent disease-dependent associations, prompted evaluation of various concentration ratios for their discriminating ability. We examined a number of different permutations and identified the following ratios as the most discriminative:

a) IGF-I/free PSA, b) intact IGFBP-3/free PSA, c) (IGF-I/total IGFBP-3)/free PSA, d) intact IGFBP-3/total IGFBP-3)/free PSA, and e) (IGF-I+intact IGFBP-3)/free PSA.

Figure 5A:
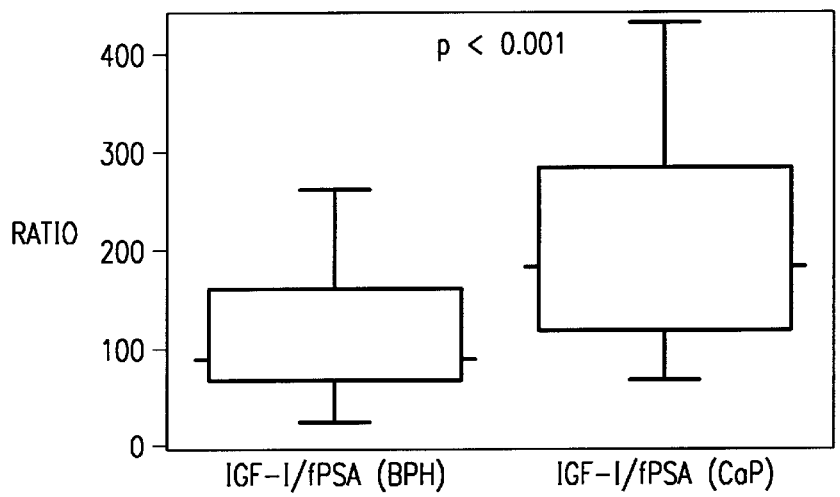
FIG. 5. Distribution of various concentration ratios in BPH and CaP patients. Box plot of IGF-I/free PSA (FIG. 5A), intact IGFBP-3/free PSA (FIG. 5B) and (IGF-I/total BP3)/free PSA (FIG. 5C) ratios in subjects with BPH and CaP. The median (centerline) and the 95% limits about the median are shown. Abbreviations are described in footnote to Table 1.
Figure 5B:
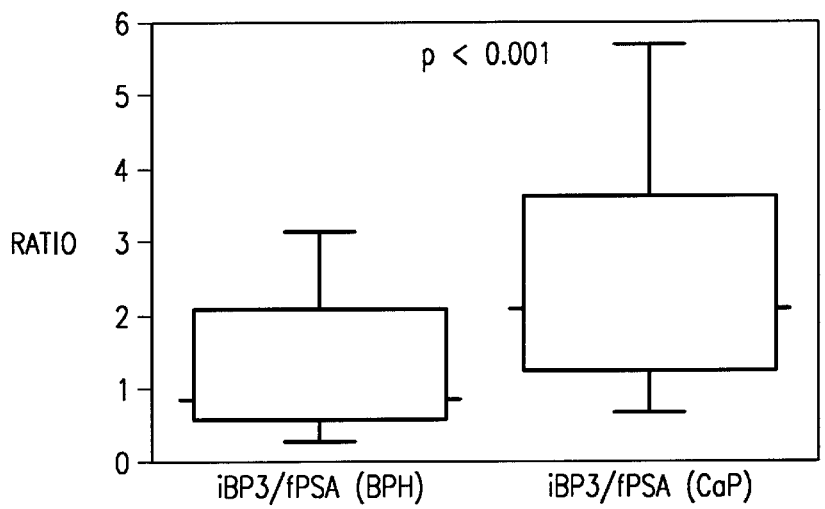
Figure 5C:
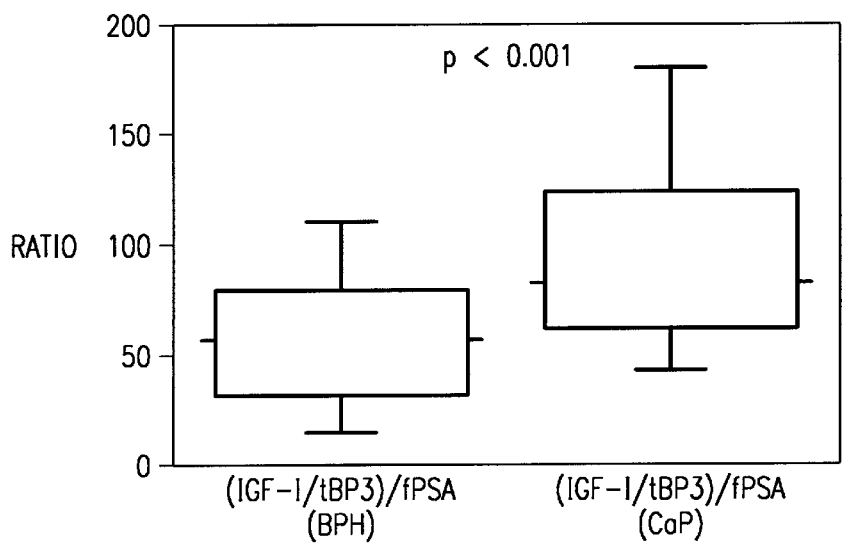
Figure 6A:
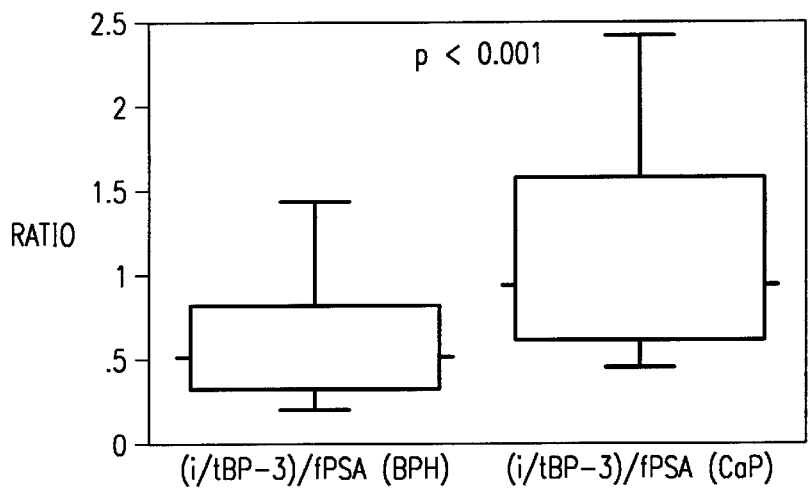
FIG. 6. Distribution of various concentration ratios in BPH and CaP patients. Box plot of intact (IGFBP-3/total IGFBP-3)/free PSA (FIG. 6A), (IGF-I+intact IGFBP-3)/free PSA (FIG. 6B), and free PSA/total PSA (FIG. 6C) ratios in subjects with BPH and CaP. The median (centerline) and the 95% limits about the median are shown. Abbreviations are described in footnote to Table 1.
Figure 6B:
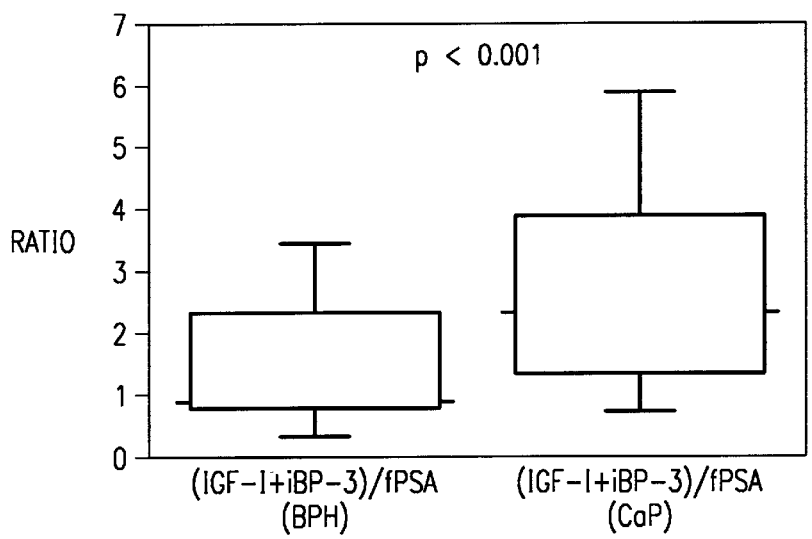
Figure 6C:
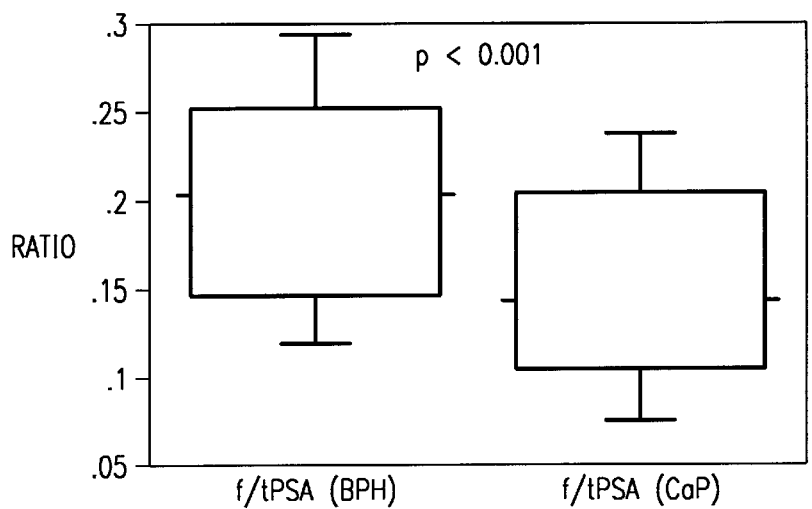
Figure 7:
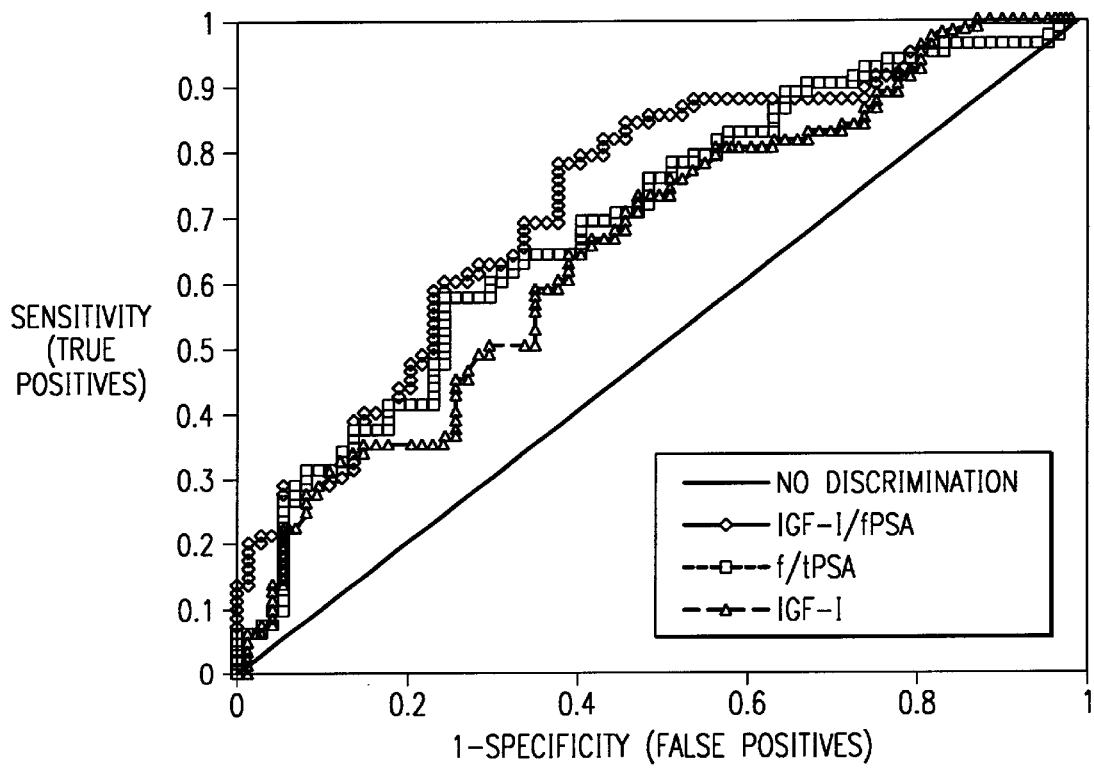
FIG. 7. Receiver operating characteristics (ROC) curves. Comparative potential of IGF-I and IGF-I/free PSA ratio relative to free PSA/total PSA ratio in discriminating between BPH and CaP patients is shown. 1—Specificity (1−[true negatives/true negatives+false positives]) versus sensitivity (true positives/true positives+false negatives) is plotted. The corresponding area under the curve (AUC) and confidence intervals (CI) are described in the text. Abbreviations are described in footnote to Table 1.
Figure 8:
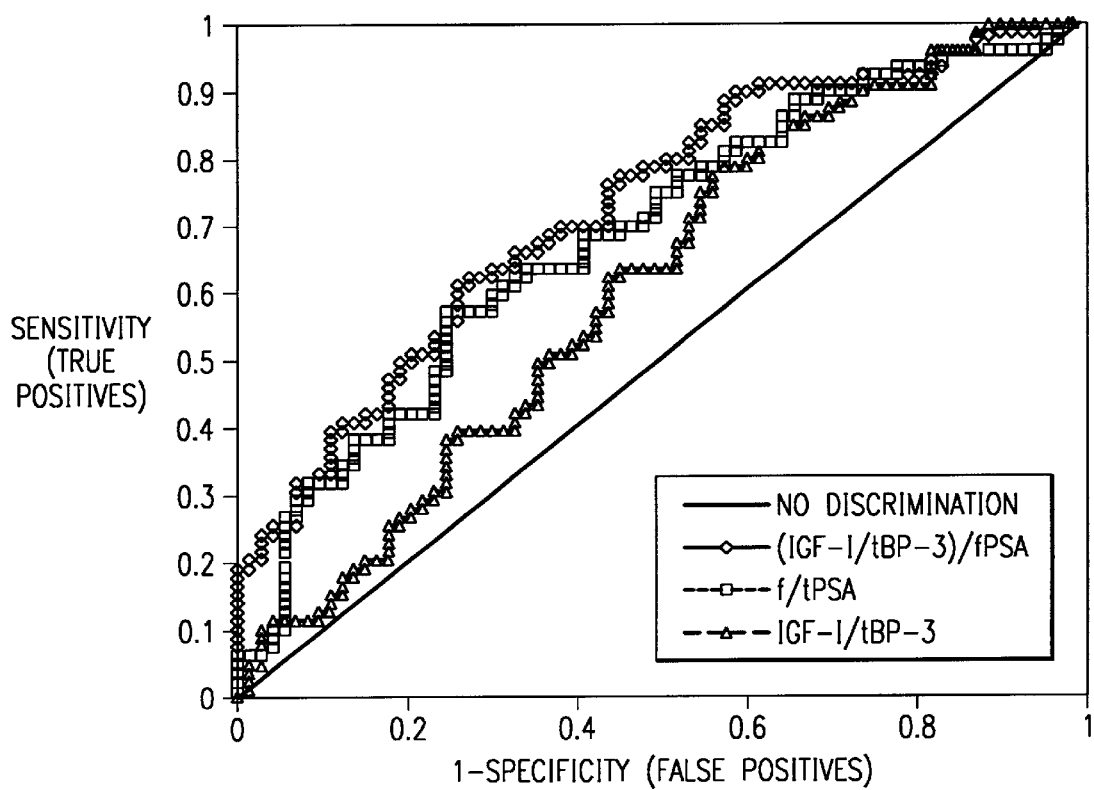
FIG. 8. Receiver operating characteristics (ROC) curves. Comparative potential of (IGF-I/total IGFBP-3)/free PSA and IGF-I/total IGFBP-3 ratios relative to free/total PSA ratio in discriminating between BPH and CaP patients is shown. 1—Specificity versus sensitivity is plotted, as in FIG. 7. The corresponding area under the curve (AUC) and confidence intervals (CI) are described in the text. Abbreviations are described in footnote to Table 1.
Figure 9:
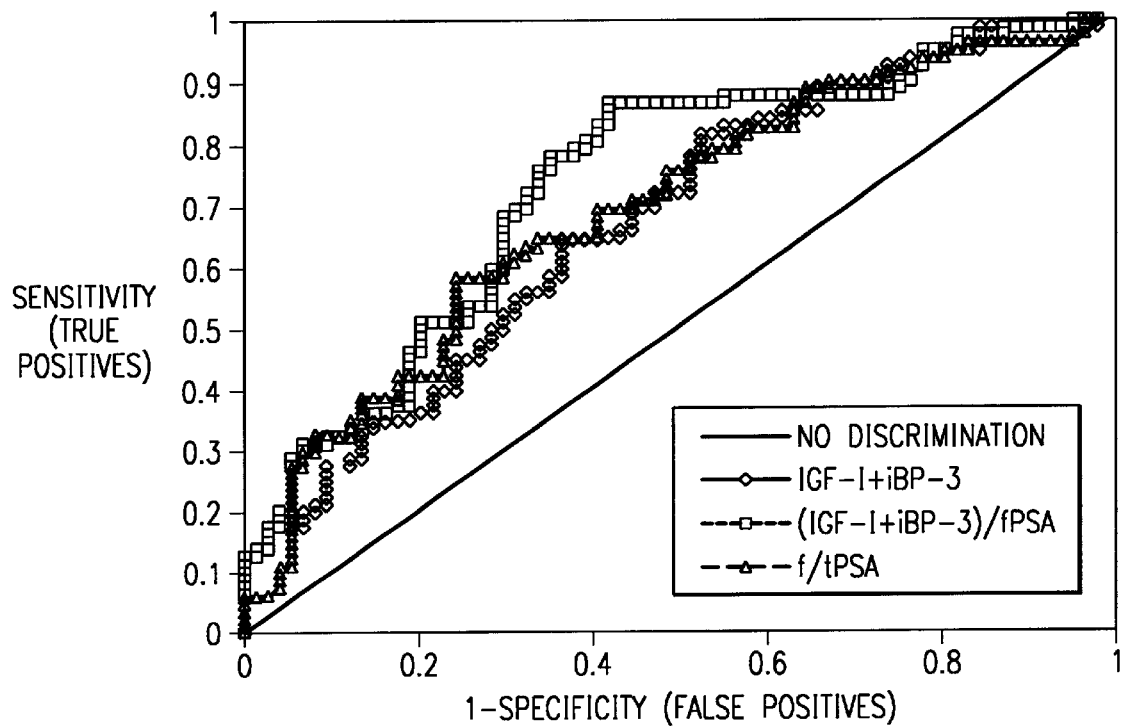
FIG. 9. Receiver operating characteristics (ROC) curves. Comparative potential of IGF-I+intact IGFBP-3 and (IGF-I+intact IGFBP-3)/free PSA ratio relative to free PSA/total PSA ratio in discriminating between BPH and CaP patients is shown. 1—Specificity versus sensitivity is plotted, as in FIG. 7. The corresponding area under the curve (AUC) and confidence intervals (CI) are described in the text. Abbreviations are described in footnote to Table 1.
Figure 10:
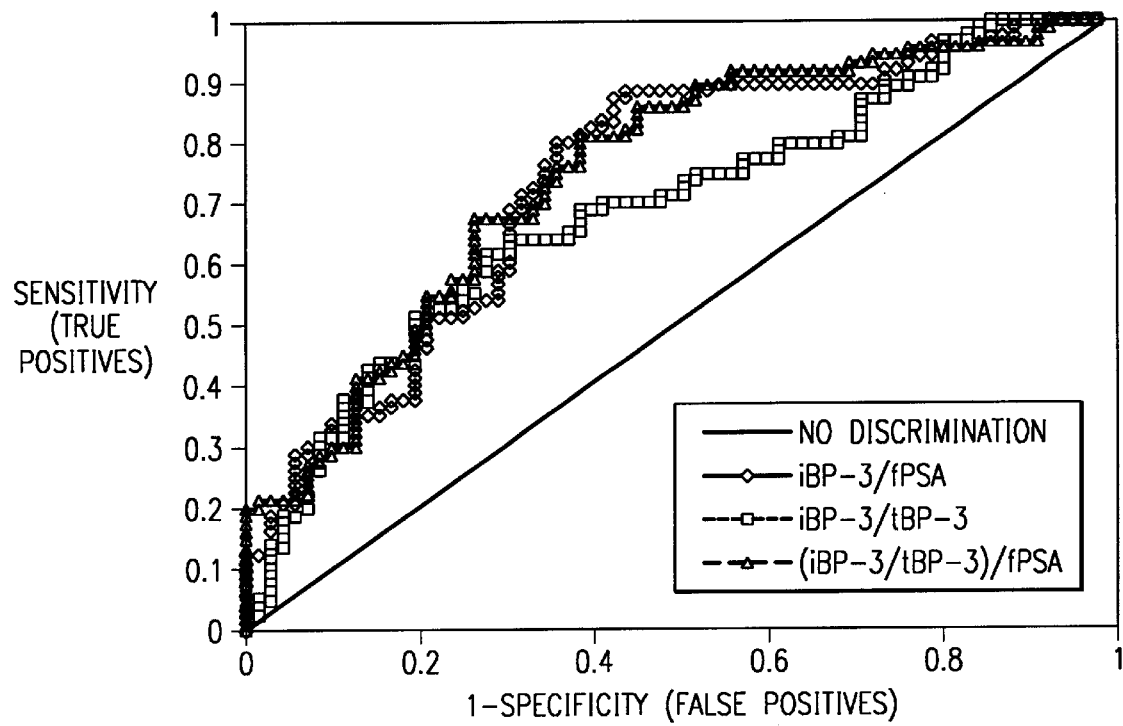
FIG. 10. Receiver operating characteristics (ROC) curves. Comparative potential of intact IGFBP-3/free PSA, intact IGFBP-3/total IGFBP-3, and (intact IGFBP-3/total IGFBP-3)/free PSA ratios in discriminating between BPH and CaP patients is shown. 1—Specificity versus sensitivity is plotted, as in FIG. 7. The corresponding area under the curve (AUC) and confidence intervals (CI) are described in the text. Abbreviations are described in footnote to Table 1.

As shown in FIGS. 5 and 6, the median values for the above ratios were significantly different in BPH vs CaP subjects, and were 94.91 and 185 (FIG. 5A), 0.85 and 2.09 (FIG. 5B), 56.26 and 82.4 (FIG. 5C), 0.489 and 0.938 (FIG. 6A), 0.978 and 2.361 (FIG. 6B). As previously reported (36, 37), the median values for free/total PSA ratio was lower in CaP than in BPH subjects and were 0.144 and 0.202 respectively (FIG. 6C).

Although the observed differences were all highly significant (p<0.001), the medians for the new parameters showed an increase of 1.46 fold (for IGF-I/total IGFBP-3)/free PSA ratio) to 2.46 fold (for intact IGFBP-3/free PSA) in CaP vs BPH subjects. The free/total PSA ratio showed a relative change of only 1.39 fold. Thus, the above ratios demonstrated increased ability to discriminate between BHP and CaP patients who have PSA levels in the gray-zone.

Receiver Operating Characteristic Curves

In attempts to better define the cancer differentiating potential of the measured and calculated parameters, receiver operating characteristics curves (ROC) were constructed. As shown in Table 3, ratios demonstrated better discriminating powers than the individual variables.

TABLE 3

Characteristics of ROC curves for measured and calculated parameters

| Function* | AUC | SE | P | 95% CI of Area |
|---|---|---|---|---|
| (f) PSA/(t) PSA | 0.689 | 0.0425 | <0.0001 | 0.605 to 0.772 |
| IGF-I | 0.655 | 0.0438 | 0.0002 | 0.569 to 0.741 |
| IGF-I/(t) PSA | 0.646 | 0.0445 | 0.0005 | 0.559 to 0.733 |
| IGF-I/(f) PSA | 0.728 | 0.0404 | <0.0001 | 0.649 to 0.808 |
| IGF-I/(t) BP-3 | 0.609 | 0.0460 | 0.0088 | 0.519 to 0.699 |
| IGF-I/(t) BP-3/(t) PSA | 0.617 | 0.0453 | 0.0049 | 0.528 to 0.706 |
| IGF-I/(t) BP-3/(f) PSA | 0.725 | 0.0405 | <0.0001 | 0.646 to 0.805 |
| (i) BP-3 | 0.663 | 0.0435 | <0.0001 | 0.578 to 0.749 |
| (f) BP-3 | 0.553 | 0.0463 | 0.1266 | 0.462 to 0.644 |
| (t) BP-3 | 0.565 | 0.0461 | 0.0791 | 0.475 to 0.655 |
| (i) BP-3/(f) PSA | 0.737 | 0.0404 | <0.0001 | 0.584 to 0.754 |
| (i) BP-3/(t) BP-3 | 0.685 | 0.0427 | <0.0001 | 0.601 to 0.769 |
| (i) BP-3/(t) BP-3/(f) PSA | 0.747 | 0.0395 | <0.0001 | 0.670 to 0.824 |
| IGF-I + (i) BP-3 | 0.670 | 0.0432 | <0.0001 | 0.585 to 0.754 |
| (IGF-I + (i) BP-3)/(f) PSA | 0.733 | 0.0405 | <0.0001 | 0.653 to 0.824 |
| IGF-IX (i) BP-3 | 0.669 | 0.0436 | <0.0001 | 0.584 to 0.755 |
| IGF-IX (i) BP-3/(f)PSA | 0.710 | 0.0419 | <0.0001 | 0.600 to 0.768 |

*Abbreviation are described in the footnote to Table 1.

Ratios involving total PSA or fragment IGFBP-3 were least discriminating, while those based on IGF-I, intact IGFBP-3 and free PSA appeared most discriminating. Compared to the currently used free/total PSA (AUC, 0.689; 95% CI, 0.605–0.772), several permutations, particularly the ratios of (intact IGFBP-3/total IGFBP-3)/free PSA, intact IGFBP-3/free PSA, (IGF-I+intact IGFBP-3)/free PSA, IGF-I/free PSA, and (IGF-I/total IGFBP-3)/free PSA demonstrated better discriminative potential (Table 3 and FIGS. 7–10) than the prior art methodology.

Among these, the (intact IGFBP-3/total IGFBP-3)/free PSA (AUC, 0.747; 95% CI, 0.670–0.824) and intact IGFBP-3/free PSA (AUC, 0.737; 95% CI, 0.585–0.745) ratios, involving intact IGFBP-3, had better differentiating power than the IGF-I/free PSA ratio (AUC, 0.728; 95% CI, 0.649–0.808). The ratios of (IGF-I+intact IGFBP-3)/free PSA (AUC, 0.733; 95% CI, 0.812) and (IGF-I/total IGFBP-3)/free PSA (AUC, 0.725; 95% CI, 0.646–0.805) were also found to have potential.

We also examined other functions involving IGF-I, intact IGFBP-3 and free PSA (logarithmic ratios, difference), but none appeared promising. The comparative ability of IGF-I/free PSA, intact IGFBP-3/free PSA, and free/total PSA ratio in differentiating between BPH and CaP patients at selected cut-off values is summarized in Table 4. The observation that the IGF-I/free PSA or intact IGFBP-3/free PSA ratio could be used to significantly improve the specificity of CaP detection is of particular importance as it complement the free/total PSA testing, which has a problem of a poor cancer detection specificity. Obviously, the inverse relation of IGF-I/free PSA or intact IGFBP-3/free PSA relative to free/total PSA testing in terms of limits of sensitivity versus specificity could potentially further enhance the diagnostic differentiation between CaP and BPH. As has been demonstrated for this particular application, the present findings further exemplify the significant clinical potential of combination testing of biomarkers that respond inversely to pathophysiological changes. The combined testing of such variables followed by data analysis by appropriate statistical manipulation may obviously help enhancing the diagnostic accuracy of disease versus non-disease identification.

TABLE 4

Comparison of sensitivity vs specificity at selective cut-off points[a]

| Parameter | Cut-off value** | Sensitivity (%) | Specificity (%) | CaP value |
|---|---|---|---|---|
| (f) PSA/(t) PSA | 0.419 | 100 | 2.7 | <cut-off |
|  | 0.28 | 95 | 17 | <cut-off |
|  | 0.24 | 90 | 27 | <cut-off |
| IGF-I/(f) PSA | 410 | 100 | 14 | >cut-off |
|  | 273 | 95 | 29 | >cut-off |
|  | 264 | 90 | 29 | >cut-off |
| (i) BP-3/(f) PSA | 5200 | 100 | 13 | >cut-off |
|  | 3500 | 95 | 29 | >cut-off |
|  | 3100 | 90 | 34 | >cut-off |

[a]Data from ROC curves
*Abbreviation are described in the footnote to Table 1.
**Values throughout for total (t) PSA, free (f) PSA, IGF-I are in $\mu g/L$; intact (i) IGFBP-3 (BP-3), fragment (f) IGFBP-3 and total (t) IGFBP-3 are in mg/L. All units are changed to mg/L and the cut-off value is therefor unitless in this table.

Univariate and Multivariate Analysis

We developed univariate and multivariate logistic regression models in attempts to further demonstrate the cancer predictive values of the new determinants. As shown in Table 5, increased levels of IGF-I/free PSA and intact IGFBP-3/free PSA ratios were found to be associated with increased probability for cancer.

TABLE 5

Univariate analysis for predicting presence of CaP using unconditional logistic regression modeling

| Covariate* | Crude risk ratio | 95% C.I. | p-value** |
|---|---|---|---|
| (t) PSA | 0.93 | 0.77–1.13 | 0.48 |
| (f) PSA | 0.28 | 0.12–0.61 | 0.0016 |
| (f) PSA/(t) PSA | 0.20 | 0.042–0.83 | 0.0038 |
| IGF-I | 2.57 | 1.16–5.73 | 0.02 |
| IGF-I/(f) PSA | 6.71 | 3.34–13.1 | <0.001 |
| (i) BP-3 | 2.63 | 1.52–4.55 | <0.001 |
| (t) BP-3 | 1.68 | 0.91–3.05 | 0.093 |
| (i) BP3/(t) BP-3 | 2.19 | 1.25–3.80 | 0.003 |
| (i) BP-3/(f) PSA | 3.30 | 1.82–5.90 | <0.001 |
| Age | 0.99 | 0.94–1.04 | 0.62 |

*Abbreviation are described in the footnote to Table 1.
**Test for trend

In multivariate analysis as shown in Tables 6 and 7, IGF-and IGFBP-3-based variables were considered separately because of the strong correlation between these parameters as well as to show their separate relation to PSA measurement. These regression models were adjusted for IGF-I/free PSA or intact IGFBP-3/free PSA, as well as for total PSA, free/total PSA, and age, all of which were considered as continuous variables. These models identified both IGF-I/free PSA (crude risk ratio=2.8, 95% CI=1.72–4.61, p<0.001) and intact IGFBP-3/free PSA (crude risk ratio=1.66, 95% CI=1.18–2.34, p<0.004) as independent factors in predicting the presence of CaP and thus, highly useful for differentiating between CaP and BPH patients. In both cases, free/total PSA ratio appear to significantly improve the predictive power of the indicator ratios in these multivariate models (Table 6 and 7).

TABLE 6

Multivariate analysis for predicting presence of CaP using unconditional logistic regression modeling

| Covariate* | Crude risk ratio | 95% C.I. | p-value** |
|---|---|---|---|
| (t) PSA | 1.05 | 0.84–1.32 | 0.66 |
| (f) PSA/(t) PSA | 0.30 | 0.15–0.66 | 0.002 |
| IGF-I/(f) PSA | 2.80 | 1.72–4.61 | <0.001 |
| Age | 1.0 | 0.97–1.10 | 0.28 |

*Abbreviations are described in the footnote to Table 1.
**Test for trend

TABLE 7

Multivariate analysis for predicting presence of CaP using unconditional logistic regression modeling

| Covariate* | Crude risk ratio | 95% C.I. | p-value** |
|---|---|---|---|
| (t) PSA | 1.06 | 0.83–1.33 | 0.65 |
| (f) PSA/(t) PSA | 0.39 | 0.16–0.82 | 0.016 |
| (i) BP-3/(f) PSA | 1.66 | 1.18–2.34 | 0.0035 |
| Age | 1.03 | 0.96–1.09 | 0.38 |

*Abbreviations are described in the footnote to Table 1.
**Test for trend

Discussion

IGFs are endocrine, paracrine, and autocrine hormone that play significant roles in cellular growth and differentiation (3, 4). Although cumulating evidence has implicated involvement of the IGF system in cellular carcinogenesis (3, 4, 11–13, 18–22), the proposed association has not been invariably confirmed. In case of the most intensely investigated prostate cancer, earlier data identified little or no difference in serum IGF-I in CaP vs normal patients (18). In addition, the high IGF-I levels as occur in acromegaly are reportedly associated with BPH but not CaP (23, 24). These differences may partly be due to the effects of population and IGF assay differences (18), and partly because acromegaly arguably results from exposure to a relatively balanced increase in the levels of both IGF-I and its major binding protein IGFBP-3, with little change in IGF-I/IGFBP-3 ratio (17, 46).

In contrast, prostate carcinogenesis might be more closely dependent on dysregulation of the IGF system, resulting in over-expression of the effector IGF-I physiology (15, 23). Predictably, regulation of the IGFs' action depends on the integrated effects of the systemic/locally produced IGFs, IGFBPs, various cell surface receptors and proteases that cleave IGFBPs and, thus, modulate their bioactivities. The profound effects of diseased/tissue-associated physiological changes and factors such as nutrition, genetics and aging on the rate of IGFs' production (3, 4, 17, 47, 48, 49) further compound this complexity. As the systemic levels of IGFs could be influenced by multiple variables, results of serum determinations may not consistently reflect disease status as long as the masking effects of non-disease influences are not carefully considered. The latter may be exemplified by the reported failure of IGF-I association with prostate and breast cancer risk in older individuals (28, 29).

Consistent demonstration of IGFs' involvement with cancer may be even more complex if dysregulation of the bioactive (tissue accessible) form of the IGFs is the most important determinant of outcome. As the bioactive form of IGFs may be difficult to accurately quantify (50), approaches involving analysis of the IGFs, relevant IGFBPs and/or various permutations thereof may better represent changes in the dynamics of the IGF regulation. The predictive power of such analytical indicator(s) could be further strengthened by their inclusion in multivariate analysis that could also involve determinations of tissue and/or tumor-specific (associated) markers.

Based on the above rational, we measured serum IGF-I and IGFBP-3 in a group of patients with BPH or CaP and who had total PSA in the diagnostic "gray zone" range. Of major interest was the investigation of intact, fragment, and total IGFBP-3 levels, as indicator of cancer-associated proteolysis, which has been long implicated in etiology of various malignancies (13, 14, 51). Among the key findings were identification of significantly higher levels of IGF-I and intact IGFBP-3 in CaP patients (p<0.001), while changes in fragment and total IGFBP-3 were statistically insignificant. The observed differences were further evident in percentile distribution plots, which consistently identified higher percentages of patients with CaP at a given IGF-I or intact IGFBP-3 level, except at the high end where the plots overlapped and, similar to those for fragment and total IGFBP-3, became non-discriminative. Confirming previous observations (36, 37), the total PSA levels were similar in the two group of patients (p=0.173), while the free PSA levels were significantly lower in CaP (p<0.001).

In comparative correlation analysis, free PSA showed negative correlation with levels of IGF-I and IGFBP-3 (intact and total) in BPH but not in CaP patients. In contrast, no correlations were found in comparisons involving total PSA. The latter may be expected as the total PSA levels quantified include its catalytically active form, which is reportedly inactivated upon release by complex formation with protease inhibitors, particularly alpha-1-antichymotrypsin (ACT) (52–54). The free form of PSA, amounting to about 10–40% of the total levels (55), is considered catalytically inactive (52–54), which our findings appear to confirm, but for CaP only. The reported higher levels of PSA binding to ACT in CaP (52–55) would theoretically protect against potential IGFBP-3 proteolysis. However, the inverse relation of free PSA with IGF-I or IGFBP-3 in BPH suggests circulation of at least a proportion of free PSA in catalytically active form in the BPH patient. This is consistent with a recent report suggesting that internal cleavage (nick) of PSA in BPH patients may be responsible for PSA's relatively lower binding to ACT as well as its lower chymotrypsin-like activity in comparison to seminal plasma PSA Interestingly, PSA in BPH patients and in seminal plasma from normal individuals had similar trypsin-like catalytic activity (54).

Whether the trypsin-like activity of free PSA in BHP patients and its inability to efficiently complex with ACT is responsible for its inverse relation to IGF-I and IGFBP-3 as demonstrated here remains to be investigated. Theoretically, IGFBP-3 proteolysis would lead to IGF dissociation, facilitating clearance and/or tissue uptake of both IGF-I and IGFBP-3 fragments and thus, a relative reduction in IGF-I and IGFBP-3 levels with increasing PSA. Our data suggest that blocking of a proportionally higher levels of catalytically active PSA by ACT, or other inhibitors, might be partly responsible for the higher systemic IGF-I and IGFBP-3 levels in CaP. This combined with possible increases in prostatic IGF-I and IGFBP-3 production may further account for their elevated levels in CaP patients. The inhibition of PSA action in cancer could reportedly involve both liver and prostatic sources of ACT (53). Whether enhanced inhibition of IGFBP-3 proteolysis at local prostatic levels would favor enhancement (or inhibition) of tumor growth will have to be clarified.

We recently reported significant association of high IGFBP-3 levels in primary breast tumor extracts with unfavorable prognostic indicators of the disease (56), and more recently found that in breast nipple aspirate fluid (NAF) IGFBP-3 levels were directly and IGFBP-3 fragment levels were inversely related to breast cancer risk (57). IGFBP-3 levels in NAF were also inversely associated with PSA. It is also noteworthy that anti-proliferative (apoptotic) properties of IGFBP-3, including ability of IGFBP-3 fragments to inhibit the mitogenic effects of IGF-I have been described (8–14).

Identification of markers with inverse relation in CaP (i.e. IGF-I and intact IGFBP-3 vs free PSA) prompted the examination of several concentration ratios and measurement permutations in relation to PSA. Among the various possibilities, permutations of total IGF-I/free PSA, intact IGFBP-3/free PSA, (IGF-I/total IGFBP-3)/free PSA, (intact IGFBP-3/total IGFBP-3)/free PSA, and (IGF-I+intact IGFBP-3)/free PSA appeared most promising. By ROC analysis, determination of total IGF-I/free PSA and intact IGFBP-3/free PSA demonstrated better discriminating potential than the currently used free PSA/total PSA ratio. Although several other permutations, notably the ratio of (intact IGFBP-3/total IGFBP-3)/free PSA showed even better discriminative power, the relative improvement may not be significant enough to warrant inclusion of a third measurement component.

The potential of growth factor/tumor marker permutations were further confirmed by multivariate analysis, which identified IGF-I/free PSA and intact IGFBP-3/free PSA as independent parameters for discriminating between BPH and CaP. As shown in Table 4, at a cutoff value of 0.28, the free/total PSA ratio identified 95% of cancer patients (false negative rate of 5%) with a specificity of 17% (false positive rate of 83%), confirming previous reported observations (36, 37). On the other hand, the IGF-I/free PSA ratio at a cut-off value of 273, identified 29% of cancer patients with a specificity of 95%. Intact IGFBP-3/free PSA at a cut-off value of 3500 also detected 29% of patients with cancer with specificity of 95%. Because the free/total PSA ratio significantly improves the predictive power of the above multivariate models, IGF-I/free PSA or intact IGFBP-3/free PSA ratios could potentially further enhance the diagnostic differentiation between CaP and BPH. As described earlier, the observation that the IGF-I/free PSA or intact IGFBP-3/free PSA ratio could be potentially used to significantly improve the specificity of CaP detection is of particular importance as it complements the free/total PSA testing, which has a problem of poor cancer detection specificity.

In summary, in a group of subjects with total PSA in the diagnostic gray-zone, we identified significantly higher IGF-I and intact IGFBP-3 levels in those patients with CaP than those with BPH. Among several possibilities, the IGF-I/free PSA and intact IGFBP-3/free PSA ratios demonstrated potential for significant CaP diagnostic improvements. As the new permutations of markers appear to compliment traditional testing (Table 4), analysis of IGF-I/free PSA or intact IGFBP-3/free PSA may further enhance the diagnostic discrimination between BPH and CaP. Further, the inclusion of additional IGF axis parameters, such as IGFBP-2, or studies of increased sample size may still further improve the discriminating power of the indicator ratios.

To our knowledge, this represents the first attempt in establishing the potential utility of IGFs and/or IGFBPs testing in relation with a tumor associated biomarker. We believe that the idea has general applicability in human cancer diagnostics and could be readily evaluated to involve other representatives of the IGF system (e.g. IGF-I and IGF-II, and IGFBP-1–9 and IGFBP related proteins). In light of these findings, application of such vertical (e.g., IGF-I/intact IGFBP-3 or IGF-I/IGFBP-2) or lateral (e.g. IGF-I/free PSA or IGFBP-2/free PSA) marker permutations may prove valuable in differential diagnosis of human cancer in general and prostate cancer in particular.

Example 2

As indicated above, the ratio of IGF-I/free PSA or intact IGFBP-3/free PSA in relation to CaP vs BPH (see Table 4) can be used as a significantly better predictive of BPH than is the currently used ratio of free/total PSA, which has a proven specificity problem. Based on the above findings, we predict that determinations of additional IGF axis components in various permutations with PSA or other tumor markers may further enhance discrimination between various cancer and benign conditions.

In addition to PSA, the kallikreins might represent a tumor marker that can be used in various permutations with IGF axis components to enhance the discriminating power of diagnostic tests. PSA and kallikreins, such as human kallikrein 2 (hK2), are members of a multigene family of serine proteases that share up to 80% sequence homology. Further, the kallikreins have been shown to be expressed in various biological fluids of normal or malignant origins (58). For example, PSA and hK2 have been detected in serum and/or tissue extract of patients with breast (59) and lung cancers (60), as well as in those with prostate cancer. Thus, we further speculate that determination of ratios of IGFs (free or total IGF-I, or IGF-II)/kallikrein or intact IGFBP-3 or other IGFBPs/kallikrein could have potential utility in the detection of various cancers.

For example, because high IGF-I levels are also associated with breast, and lung cancers, one might predict that the indicator ratios described herein (with or without a tumor marker such as PSA or a kallikrein) would also be useful predictors for these conditions. In contrast, over-expression of both IGF-I and IGF-II has been linked to colorectal cancers. Thus, it might be predicted that and IGF-I X IGF-II or IGF-I+IGF-II, alone or taken together with a measurement of a suitable tumor marker (such as CA-19.9), would provide increased predictive power of colorectal cancers over current methodologies.

Similarly we predict that determination of the ratios of IGFs (IGF-I or IGF-II) or IGFBPs (IGFBP-1–6 and/or IGFBP-RP-1–9) in relation to PSA or kallikrein proteins (or other tumor markers) would have increased discriminating power in the differential diagnosis of prostate, breast and lung and possibly other cancers. As exemplified for prostate cancer, determination of IGF/IGFBP ratios could be of significant clinical value in other human cancers, such as cancer of the breast, colorectal, and lung cancers. Although a PSA-equivalent marker for these cancers has not been described as yet, we predict that measurement of the concentration ratio of IGF-I and/or IGF-II (free or total) in relation to IGFBPs (IGFBP-1, IGFBP-2, IGFBP-3, IGFBP4, IGFBP-5, IGFBP-6) could be useful in differentiating cancerous from non-cancerous disease.

We further predict that ratios of IGF-I or IGF-II (free or total) in relation to IGFBP related protein (IGFBP-rPs1–9) which share significant N-terminal homology with the classical IGFBPs (IGFBP-1–6), but bind IGFs with lower affinity, could be also of significant clinical value. To date up to nine different IGFBP-related binding proteins (IGFBPrP-1–9) have been identified (5), and additional IGFBP-rPs will most probably be discovered. For example, in the case of the prostate cancer, ratios of IGF-I/IGFBP-rP-1, or ratio of intact IGFBP-3/1IGFBP-rP-1 might prove to be very useful. The same may be also true for other human cancers which may benefit from determinations of ratios of IGF-I or IGF-II (free or total)/IGFBP-rPs. In this context, determinations of IGFBP-2/IGF-I, or IGFBP-2/IGF-II may be of significant clinical value in relation to colon cancer, while ratios of IGFBP-2/IGFBP-rP-1 might have diagnostic value in breast tumor.

We further speculate that the circulating levels of the IGF superfamily of molecules (5) might be a surrogate marker (18) of the tissue levels (e.g. prostate, breast and colon) of these variables. If this prediction is true, then identification of markers with statistically significant but weak association with a given cancer at serum level (as a result of blood volume dilution effect) could lead to identification of markers with significantly stronger and more distinct association with the cancer at the tissue level. If the serum/tissue relation is correct, then measurement of the IGF axis components and one or more tumor markers at the tissue level (e.g. by immunohistochemical staining and electron microscopy, or in tumor cell extracts) might be also highly beneficial.

Of course, we realize that this general approach of combining IGF axis component measurements together with a tumor marker measurement would require systematic evaluation of the effect of the various markers and their permutations as described above, using several of the currently available mathematical regression modeling. The latter could be readily performed in the hand of an expert statistician and a good computer software (such as that described above). Experiments are planned to test and confirm the above predictions.

REFERENCES

The following citations are hereby incorporated by reference into this specification.

1. Lamson G, Giudice L, Rosenfeld R. 1991 Insulin-like growth factor binding proteins: Structural and molecular relationships [review]. Growth Factors 5:19–28.
2. Cohen P, Rosenfeld R G. 1994 Physiologic and clinical relevance of the insulin-like growth factor binding proteins [review]. Curr Opin Pediatr 6:462467.
3. Jones J I, Clemmons D R. 1995 Insulin-like growth factors and their binding proteins: Biological Actions [review]. Endocrin Rev 16:3–34.
4. Rajram S, Baylink D J, Mohan S. 1997 Insulin-like growth factor-binding proteins in serum and other biological fluids: regulation and functions [review]. Endocrin Rev 18:801–831.
5. Hwa V, Oh Y, Rosenfeld R G. 1999 Insulin-like growth factor binding proteins: a proposed superfamily. Acta Paediatr Suppl 88:37–45.
6. Kelley K M, Oh Y, Gargosky S E, Guecv Z, Matsumoto T, Hwa V, Ng L, Simpson D M, Rosenfeld R G. 1996 Insulin-like growth factor-binding proteins (IGFBPs) and their regulatory dynamics. Intl Biochem Cell Biol 28:619–637.
7. Ferry Jr R I, Cerri R W, Cohen P. 1999 Insulin-like growth factor binding proteins: New proteins, new functions. Horm Res 51:53–67
8. Rechler M M. 1997 Editorial: Growth inhibition by insulin-like growth factor (IGF) binding protein-3— What's IGF got to do with it. Endocrinology 138:2645–47.
9. Valentinis B, Bhala A, Deangelis T, Baserga R, Cohen P. 1995 The human insulin-like growth factor (IGF) binding protein-3 inhibits the growth of fibroblasts with a targeted disruption of the IGF-I receptor gene. Mol Endocrinol 9:361–367.
10. Zadeh S M, Binoux M. 1997 The 16-kDa proteolytic fragment of insulin-like growth factor (IGF) binding protein-3 inhibits the mitogenic action of fibroblasts growth factor on mouse fibroblasts with a targeted disruption of the type-1 IGF receptor gene. Endocrinology 138:3069–3072.
11. Rajah R, Valentinis B, Cohen P. 1997 Insulin-like growth factor-binding protein-3 induces apoptosis and mediates the effects of transforming growth factor-b on programmed cell death through a p53- and IGF-Independent mechanisms. J Biol Chem 272:12181–12188.
12. Oh Y. 1998 IGF-Independent regulation of breast cancer growth by IGF binding proteins. Breast Cancer Res Treat 47:283–293.
13. Rajah R, Katz L, Nunn S, Solberg P, Beers T, Cohen P. 1995 Insulin-like growth factor binding protein (IGFBP) proteases: Functional regulations of cell growth. Prog Growth Factor Res 6:273–284.
14. Giudice L C. 1995 Editorial: IGF binding protein-3 protease regulation: How sweet it is. J Clin Endocrinol Metab 80:2279–2281.
15. Russell P J, Bennett S, Stricker P. 1998 Growth factor involvement in progression of prostate cancer [review]. Clin Chem 44:705–723.
16. Holly Jeff. 1998 Insulin-like growth factor and new opportunities for cancer prevention. Lancet 351:1373–1374.
17. Rosen C J, Pollak M. 1999 Circulating IGF-I: New perspectives for a new century [review]. TEM 10:136–141.
18. Cohen P. 1998 Serum insulin-like growth factor-I levels and prostate cancer risk-Interpreting the evidence. J Natl Cancer Inst 90:876–879.
19. Baserga R. 1995 The insulin-like growth factor I receptor: a key to tumor growth? Cancer Res 55:249452.
20. Li S L, Goko H, Xu Z D, Kimura G, Sun Y, Kawachi M H, Wilson T G, Wilczynski S, Fujita-Yamaguchi Y. 1998 Expression of insulin-like growth factor (IGF)-II in human prostate, breast, bladder, and paraganglioma tumors. Cell Tissue Res 291:469–479.
21. Glick R P, Lichtor T, Unterman T G. 1997 Insulin-like growth factors in central nervous system tumors. J neurooncol 35:315–3125,
22. Lahm H, Amstad P, Wyniger J, Yilmaz A, Fischer J R, Schreyer M, Givel J C. 1994 Blockade of the insulin-like growth factor-I receptor inhibits growth of human colorectal cancer cells: evidence of a functional IGF-II-mediated autocrine loop. Int J Cancer 58:452–459.
23. Grimberg A, Cohen P. 1999 Growth hormone and prostate cancer: guilty by association? J Endocrinol Invest 22:64–73.
24. Colao A, Marzullo P, Spiezia S, Ferone D, Giaccio A, Cerbone G, Pivonello R, Di Somma C, Lombardi G. 1999 Effects of growth hormone (GH) and insulin-like growth factor I on prostate diseases: an ultrasonographic and endocrine study in acromegaly, GH deficiency, and healthy subjects. J Clin Endo Metab 84:1986–1991.
25. Cats A, Dullaart R P, Kleibeuker J K, Kuipers F, Sluiter W J, Hardonk M J, de vires E G. 1996 Increased epithelial cell proliferation in the colon of patients with acromegaly. Cancer Res 35 56:523–526.
26. Orme S M, Mcnally R J, Cartwright R A, Belchetz P E. 1998 Mortality and cancer incidence in acromegaly: a retrospective cohort study. United Kingdom Acromegaly Study Group. I Clin Endo Metab 83:2730–2734.

27. Chan J M, Stampfer M J, Giovannucci E, Gann P H, Ma J, Wilkinson P, Hennekens C H, Pollak M. 1998 Plasma insulin-like growth factor-I and prostate cancer risk: A prospective study. Science 279:563–566.
28. Hankinson S E, Willett W C, Colditz G A, Hunter D J, Michaud D S, Deroo B, Rosner B, Speizer F E, Pollak M. 1998 Circulating concentrations of insulin-like growth factor-I and risk of breast cancer. The Lancet 351:1393–1396.
29. Wolk A, Mantzoros C S, Andersson S-O, Bergstrom R, Signorello L B, Lagiou P, Adami H-O, Trichopoulos D. 1998 Insulin-like growth factor-I and prostate cancer risk: a population-based, case control study. J Natl Cancer Inst 90:911–915.
30. Yu H, Spitz M R, Mistry J, Gu J, Hong W K, Wu X. 1999 Plasma levels of insulin-like growth factor-I and lung cancer risk: a case-control analysis. J Natl Cancer Inst 91:151–156.
31. Manousos O, Souglakos J, Bosetti C, Tzbnou A, Chatzdakis V, Trichopoulos D, Adami HO, Mantzoros C. 1999 IGF-I and IGF-II in relation to colorectal cancer. Int J Cancer 83:15–17.
32. Cohen P, Graves H C, Peehl D M, Kamarei M, Giudice L C, Rosenfeld R G. 1992 Prostate-specific antigen (PSA) is an insulin-like growth factor binding protein-3 protease found in seminal plasma. J Clin Endocrinol Metab 75:1046–1053.
33. Carter H B, Coffey D S. 1990 The prostate: an increasing medical problem. Prostate 16:39–48.
34. Diamandis E P. 1998 Prostate specific antigen—its usefulness in clinical medicine. Trends Endocrinol Metab 9:310–316
35. Catalona W J, Smith D S, Ornstein D K. 1997 Prostate cancer detection in men with serum PSA concentrations of 2.6–4.0 ng/mL and benign prostate examination. Enhancement of specificity with free PSA measurements. JAMA 277:1452–1455.
36. Luderer A A, Chen Y T, Soriano T F, Kramp W J, Carlson G, Cuny C, Sharp T, Smith W, et al. 1995 Measurement of the proportion of free to total prostate-specific antigen improves diagnostic performance of prostate-specific antigen in the diagnostic gray zone of total prostate-specific antigen. Urology 46:187–194.
37. Catalona W J, Partin A W, Slawin K M, Brawer M K, Flanigan R C, Patel A, Richie J P, deKernion J B, et al. 1998 Use of percentage of free prostate-specific antigen to enhance differentiation of prostate cancer from benign prostate disease: a prospective multicenter clinical trial. JAMA 279:1542–1547.
38. Khosravi M J, Diamandi A, Mistry J, Lee P D K. 1996 A non-competitive ELISA for human serum insulin-like growth factor-I. Clin Chem 42:1147–1154.
39. Lee P K D, Mistry J, Hintz R L. 1996 Active insulin-like growth factor-I (IGF-I) assays. Webster: Diagnostic Systems Laboratories.
40. Yu H, Mistry J, Nicar M J, Khosravi M J, Diamandis A, Doorn J V, Jull A. Insulin-like growth factors (IGF-I, Free IGF-I, and IGF-II) and insulin-like growth factor binding proteins (IGFBP-2, IGFBP-3, IGFBP-6, and ALS) in blood circulation. 1999 J Clin Lab Analysis 13:166–172.
41. Khosravi J, Diamandi A, Mistry J, Krishna R G. 1999 The high molecular weight insulin-like growth factor binding protein complex: Epitope mapping, immunoassay, and preliminary clinical evaluation. J Clin Endocrinol Metab 84:2826–2833.
42. Khosravi M J, Diamandi A, Mistry J. 1997 Immunoassay of insulin-like growth factor binding protein-1. Clin Chem 43:523–532.
43. Diamandi A, Mistry J, Khosravi M J. Specificity of new immunoassays for human insulin-like growth factor binding protein-3 (IGFBP-3). Proc of the 80$^{th}$ Annual Meet of the Endocrine Soc. 1998; P3-360.
44. Diamandi A, Mistry J, Krishna R G, Khosravi M J. 1999 Immunoassay of insulin-like growth factor binding protein-3: New means to quantifying IGFBP-3 proteolysis. I Clin Endocrinol Metab (submitted).
45. Woodrum D L, French C M, Hill T M, Roman S J, Slatore H L, Shaffer J L, York L G, Eure K L, Loveland K G, Gasior G H, Southwick P C, Shamel B. 1997 Analytical performance of the Tandem-R free PSA immunoassay measuring free prostate-specific antigen. Clin Chem 43:1203–1208.
46. Juul A, Main K, Blum W F, Lindholm, J, Ranke M B, and Shakkeback N E. 1994 The ratio between serum levels of insulin-like growth factor (IGF)-I and the IGF binding proteins (IGFBP)-1, 2, and 3 decreases with age in healthy adults and is increased in acromegalic patients. Clin Endocrinol 41:85–93.
47. Thiissen J P, Ketelslegers J M, Underwood L E. 1994 Nutritional regulation of the insulin-like growth factors. Endocr Rev 15:80–101.
48. Harrela M, Koistinen H, Kapiro J, Lehtovirta M, Tuomilehto J, Erikisson J, Toivanen L, Koskenvuo M, Leinonen P, Koistinen R, Seppala M. 1996 Genetics and environmental components of interindividual variation in circulating levels of IGF-I, IGF-II IGFBP-1, and IGFBP-3. J Clin Invest 98:2612–2615.
49. Kao . P C, Matheny A P, Lang C A. 1994 IGF-I comparisons in healthy twin children. J Clin Endocrinol Metab. 78:310–312.
50. Khosravi M J, Diamandis A, Mistry J. 1998 Factors influencing immunoassay levels of free insulin-like growth factors (IGFs) as determined by new ELISAs. Proc of the 80$^{th}$ Annual Meet of the Endocrine Soc. 1998; P3–355.
51. Baciuchka M, Remacle-Bonnet M, Garrouste F, Favre R, Sastre B, Pommier G. 1998 Insulin-like growth factor (IGF)-binding protein-3 (IGFBP-3) proteolysis in patients with colorectal cancer: possible association with the metastatic potential of the tumor. Int J Cancer 79:460–467.
52. Stenman U-H, Leinonen J, Alfthan H, Rannikko S, Tukhanen K, Alfthan O. 1991 A complex between prostate-specific antigen and Alpha 1-antichymotrypsin is the major form of prostate-specific antigen in serum of patients with prostatic cancer: Assay of the complex improves clinical sensitivity for cancer. Cancer Res 51:222–226.
53. Cho N H, Park C, Park D S. 1997 Expression of alpha 1-antichymotrypsin in prostate carcinoma. J Korean Med Sci. 12:228–33.
54. Chen Z, Chen H, Stamey T A. 1997 Prostate specific antigen in benign prostatic hyperplasia: purification and characterization. J Urol 157:2166–70.
55. Diamandis E P. 1998 Prostate specific-antigen—its usefullness in clinical medicine. Trends Endocrinol Metab 9:310–316.
56. Yu H, Levesque M A, Khosravi M J, Papanastasiou-Diamandi A, Clark G M, Diamandis E P. 1998 Insulin-like growth factor binding protein-3 and breast cancer survival. Int J Cancer. 79:624–628.
57. Sauter E R, Litwin S, Engstrom P F, Diamandis A, Khosravi J, Diamandis E P. 1999 Insulin-like growth factor binding protein-3 (IGFBP-3) is associated with breast cancer risk. Cancer Epidemiolog Biomarkers and Prev (submitted).

58. Youse G M, Obiezu C V, Luo L Y, Black M H, Diamandis E P. Prostase/KLK-1 is a new member of the human kallikrein gene family, is expressed in prostate and breast tissues, and is hormonally regulated. Cancer Res. 59:42524256, 1999.
59. Borchert G H, Yu H, Tomlinson G, Giai M, Roagna R, Ponzone R, Sgro L, Diamandis E P. Prostate specific antigen molecular forms in breast cyst fluid and serum of women with fibrocystic breast disease J Clin Lab Anal 13:75–81, 1999.
60. Zarghami N, D'costa M, Tsuyuki D, Asa S L, Diamandis E P. Expression of the prostate-specific antigen by lung tissue. Clin Cancer Res 3:1201–6, 1997.

We claim:

1. A diagnostic method for discriminating between benign prostate disorders and prostate cancer in an individual, comprising:
   collecting a body fluid from the individual;
   measuring a free prostate specific antigen (free PSA) concentration;
   measuring an insulin-like growth factor I (IGF-I) concentration;
   measuring an insulin-like growth factor binding protein 3 (IGFBP-3) concentration;
   and calculating an indicator ratio of (intact IGFBP-3/total IGFBP-3)/free PSA based upon at least two of the measured concentrations,
      wherein the indicator ratio provides a means for discriminating between benign prostate disorders and prostate cancer.

2. A diagnostic method for discriminating between benign prostate disorders and prostate cancer in an individual, comprising:
   collecting a body fluid from the individual;
   measuring a free prostate specific antigen (free PSA) concentration;
   measuring an insulin-like growth factor I (IGF-I) concentration;
   measuring an insulin-like growth factor binding protein 3 (IGFBP-3) concentration;
   and calculating an indicator ratio of intact IGFBP-3/free PSA based upon at least two of the measured concentrations,
      wherein the indicator ratio provides a means for discriminating between benign prostate disorders and prostate cancer.

3. A diagnostic method for discriminating between benign prostate disorders and prostate cancer in an individual, comprising:
   collecting a body fluid from the individual;
   measuring a free prostate specific antigen (free PSA) concentration;
   measuring an insulin-like growth factor I (IGF-I) concentration;
   measuring an insulin-like growth factor binding protein 3 (IGFBP-3) concentration;
   and calculating an indicator ratio of (IGF-I+intact IGFBP-3)/free PSA based upon at least two of the measured concentrations,
      wherein the indicator ratio provides a means for discriminating between benign prostate disorders and prostate cancer.

4. A diagnostic method for discriminating between benign prostate disorders and prostate cancer in an individual, comprising:
   collecting a body fluid from the individual;
   measuring a free prostate specific antigen (free PSA) concentration;
   measuring an insulin-like growth factor I (IGF-I) concentration;
   measuring an insulin-like growth factor binding protein 3 (IGFBP-3) concentration;
   and calculating an indicator ratio of IGF-I/free PSA based upon at least two of the measured concentrations,
      wherein the indicator ratio provides a means for discriminating between benign prostate disorders and prostate cancer.

* * * * *

UNITED STATES PATENT AND TRADEMARK OFFICE
CERTIFICATE OF CORRECTION

PATENT NO.      : 6,448,086 B1
DATED           : September 10, 2002
INVENTOR(S)     : M. Javad Khosravi et al.

It is certified that error appears in the above-identified patent and that said Letters Patent is hereby corrected as shown below:

<u>Column 9,</u>
Line 18, replace "0.824" with -- 0.812 --
Line 41, replace "95% Cl," with -- 0.653 --

<u>Column 10,</u>
Line 51, replace "IGF-and" with -- IGF-I and --

<u>Column 14,</u>
Line 59, replace "IGFBP4" with -- IGFBP-4 --

Signed and Sealed this

Twenty-ninth Day of April, 2003

JAMES E. ROGAN
*Director of the United States Patent and Trademark Office*